(12) United States Patent
Edwards et al.

(10) Patent No.: US 8,216,237 B2
(45) Date of Patent: Jul. 10, 2012

(54) INTRAMEDULLARY DEVICE ASSEMBLY AND ASSOCIATED METHOD

(76) Inventors: Scott G. Edwards, McLean, VA (US); Ronald Arthur Yapp, Manchester, MI (US)

( * ) Notice: Subject to any disclaimer, the term of this patent is extended or adjusted under 35 U.S.C. 154(b) by 318 days.

(21) Appl. No.: 12/478,576

(22) Filed: Jun. 4, 2009

(65) Prior Publication Data
US 2010/0312244 A1 Dec. 9, 2010

(51) Int. Cl.
*A61B 17/56* (2006.01)
*A61B 17/58* (2006.01)
*A61F 2/30* (2006.01)

(52) U.S. Cl. ........................................................ 606/62

(58) Field of Classification Search ............... 606/62–68, 606/95–96, 99, 104, 86 R
See application file for complete search history.

(56) References Cited

U.S. PATENT DOCUMENTS

| | | | |
|---|---|---|---|
| 3,334,624 | A | 8/1967 | Schneider et al. |
| 4,091,806 | A | 5/1978 | Aginsky |
| 4,103,683 | A | 8/1978 | Neufeld |
| 4,875,474 | A | 10/1989 | Border |
| 4,911,153 | A | 3/1990 | Border |
| 4,981,481 | A | 1/1991 | Kranz et al. |
| 5,013,317 | A | 5/1991 | Cole et al. |
| 5,030,222 | A | 7/1991 | Calandruccio |
| 5,057,110 | A | 10/1991 | Kranz et al. |
| 5,100,404 | A | 3/1992 | Hayes |
| 5,108,398 | A | 4/1992 | McQueen et al. |
| 5,219,174 | A | 6/1993 | Zurbrugg et al. |
| 5,284,313 | A | 2/1994 | Hallgren |
| 5,352,228 | A | 10/1994 | Kummer |
| 5,472,444 | A | 12/1995 | Huebner et al. |
| 5,484,446 | A | 1/1996 | Burke et al. |

(Continued)

FOREIGN PATENT DOCUMENTS

FR 2 808 182 A1 11/2001

(Continued)

OTHER PUBLICATIONS

S.S.T.® *Small Bone Locking Nail; Forearm Nail; Surgical Technique*; Biomet Inc.; 1998; 24 pages.

(Continued)

*Primary Examiner* — Eduardo C Robert
*Assistant Examiner* — Jacqueline Johanas
(74) *Attorney, Agent, or Firm* — Alston & Bird LLP

(57) ABSTRACT

An intramedullary device for repairing defects of a bone is provided. The intramedullary device is configured to be inserted into the medullary canal of a bone and includes a stud protruding from the end. The stud includes a portion that is tapered from a first cross-sectional area to a second cross-sectional where the second cross-sectional area is smaller than that of the first cross-sectional area and the second cross-sectional area defines a region of concentrated stress. The stud also includes a portion configured to engage the internal threads of a fastener retained within an intramedullary device assembly, such as a guide member adapter. The external threads of the stud engage the internal threads of the fastener to secure the intramedullary device to the intramedullary assembly when a first torque is applied to the fastener. Upon completion of insertion, compression, and securing of the intramedullary device in the medullary canal of a bone, the intramedullary device can be separated from the intramedullary device assembly by applying a second, greater torque to the internally-threaded fastener, whereby the stud breaks at the region of concentrated stress.

18 Claims, 17 Drawing Sheets

U.S. PATENT DOCUMENTS

| | | | |
|---|---|---|---|
| 5,665,086 | A | 9/1997 | Itoman et al. |
| 5,766,174 | A | 6/1998 | Perry |
| 5,776,194 | A | 7/1998 | Mikol et al. |
| 5,779,705 | A | 7/1998 | Matthews |
| 5,910,143 | A | 6/1999 | Cripe et al. |
| 5,951,561 | A | 9/1999 | Pepper et al. |
| 6,039,742 | A | 3/2000 | Krettek et al. |
| 6,120,504 | A | 9/2000 | Brumback et al. |
| 6,183,477 | B1 | 2/2001 | Pepper |
| 6,379,360 | B1 | 4/2002 | Ackeret et al. |
| 6,443,954 | B1 | 9/2002 | Bramlet et al. |
| 6,569,165 | B2 | 5/2003 | Wahl et al. |
| 6,783,529 | B2 | 8/2004 | Hover et al. |
| 6,786,908 | B2 | 9/2004 | Hover et al. |
| 6,808,527 | B2 | 10/2004 | Lower et al. |
| 6,932,819 | B2 | 8/2005 | Wahl et al. |
| 7,033,363 | B2 | 4/2006 | Powell |
| 7,056,322 | B2 | 6/2006 | Davison et al. |
| 7,066,943 | B2 | 6/2006 | Zirkle, Jr. |
| 7,144,399 | B2 | 12/2006 | Hayes et al. |
| 7,182,765 | B2 * | 2/2007 | Roth et al. ............ 606/62 |
| 2002/0068938 | A1 * | 6/2002 | Jackson ................ 606/61 |
| 2003/0004513 | A1 * | 1/2003 | Guzman et al. ........ 606/62 |
| 2003/0135211 | A1 | 7/2003 | Cho |
| 2004/0039383 | A1 * | 2/2004 | Jackson ................ 606/61 |
| 2006/0069391 | A1 * | 3/2006 | Jackson ................ 606/62 |
| 2006/0142778 | A1 | 6/2006 | Dees, Jr. |
| 2007/0005065 | A1 * | 1/2007 | Fernandez Dell'Oca ........ 606/62 |
| 2007/0100343 | A1 | 5/2007 | Cole et al. |
| 2007/0173833 | A1 * | 7/2007 | Butler et al. ............ 606/61 |
| 2007/0190490 | A1 * | 8/2007 | Giorno ................ 433/173 |
| 2007/0219636 | A1 * | 9/2007 | Thakkar ................ 623/18.11 |
| 2007/0276382 | A1 | 11/2007 | Mikhail et al. |
| 2008/0091212 | A1 * | 4/2008 | Dwyer et al. ........... 606/99 |
| 2008/0147066 | A1 | 6/2008 | Longsworth et al. |
| 2008/0264109 | A1 | 10/2008 | Ritchey et al. |
| 2008/0269744 | A1 | 10/2008 | Kay et al. |
| 2009/0112209 | A1 | 4/2009 | Parrott et al. |
| 2009/0248024 | A1 * | 10/2009 | Edwards et al. ........ 606/62 |
| 2009/0254125 | A1 * | 10/2009 | Predick ............... 606/264 |
| 2011/0160728 | A1 * | 6/2011 | Blitz et al. ........... 606/64 |

FOREIGN PATENT DOCUMENTS

| | | |
|---|---|---|
| WO | WO 03/059181 A1 | 7/2003 |
| WO | WO 2009/139758 A2 | 11/2009 |

OTHER PUBLICATIONS

S.S.T.® *Small Bone Locking Nail; Fibula Nail; Surgical Technique;* Biomet Inc.; 1998; 12 pages.

Dragovich, Steve; *SPC, FMEA—When it Comes to Titanium Implants, it Doesn't Mean a Thing Unless the Deburring is Controlled;* Implant Manufacturing; BONEZone; Fall 2003; pp. 9-10.

Technique Guide; *The Olecranon Osteotomy Nailing System;* Synthes; Nov. 8, 2007 5:02 PM; 21 pages.

Knowles Pins from DePuy Orthopaedics, Inc.; *Medcompare™ The Buyer's Guide for Medical Professionals;* 3 pages; located at http://www.medcompare.com/details/34185/Knowles-Pins.html.

*Ankle Arthrodesis Nail—Surgical Technique;* 2000; 20 pages; Biomet Inc.; available at <http://ww.biomet.co.uk/medhome-uk/trauma/internal-fixation/ankle-arthrodesis-nail> (visited Sep. 29, 2008).

George E. Quill, Jr., M.D.; *The Use of a Second Generation Intramedullary Nail in Fixation of Difficult Ankle and Hindfoot Arthrodeses;* 10 pages; available at <http://www.louortho.com/documents> (visited Sep. 29, 2008).

International Search Report and Written Opinion for Application No. PCT/US2010/034160 mailed Aug. 23, 2010.

* cited by examiner

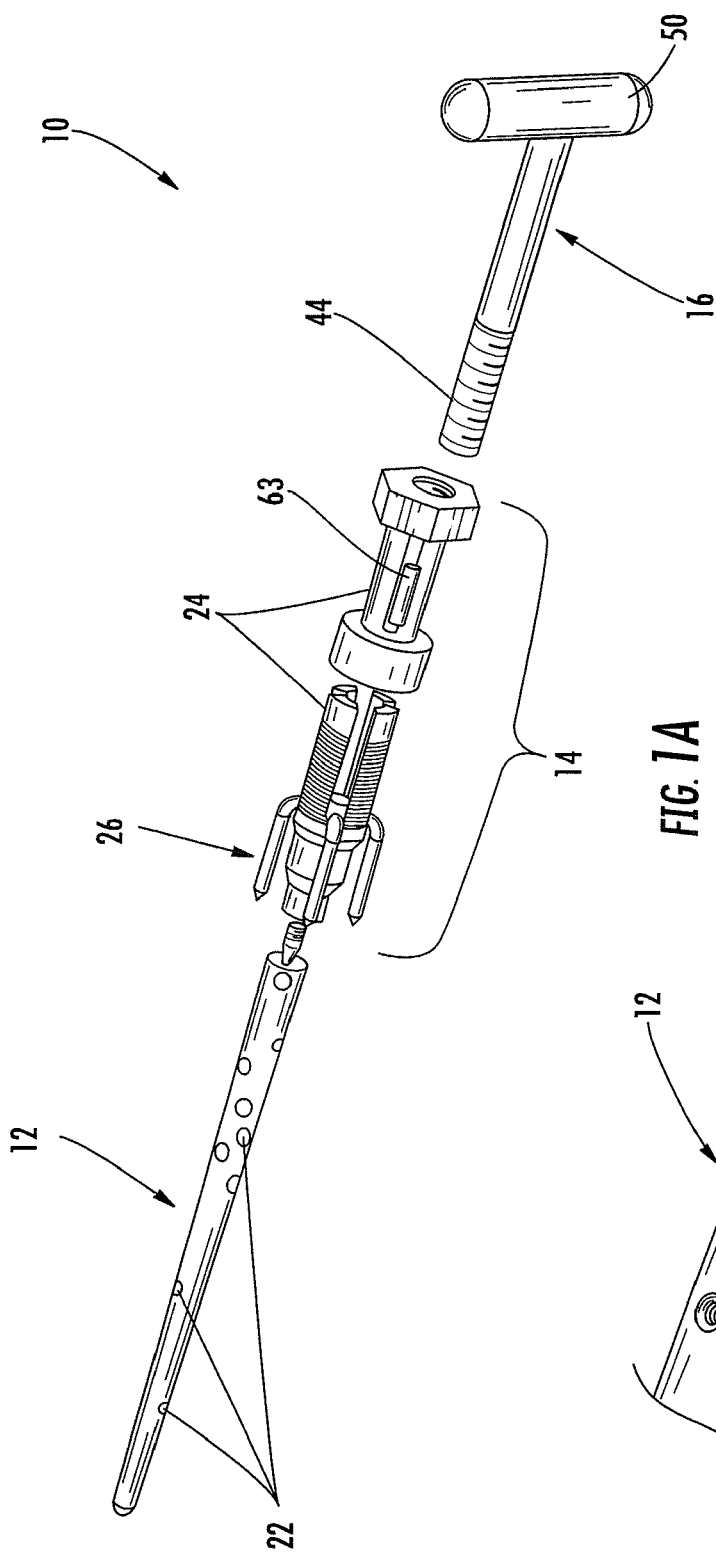

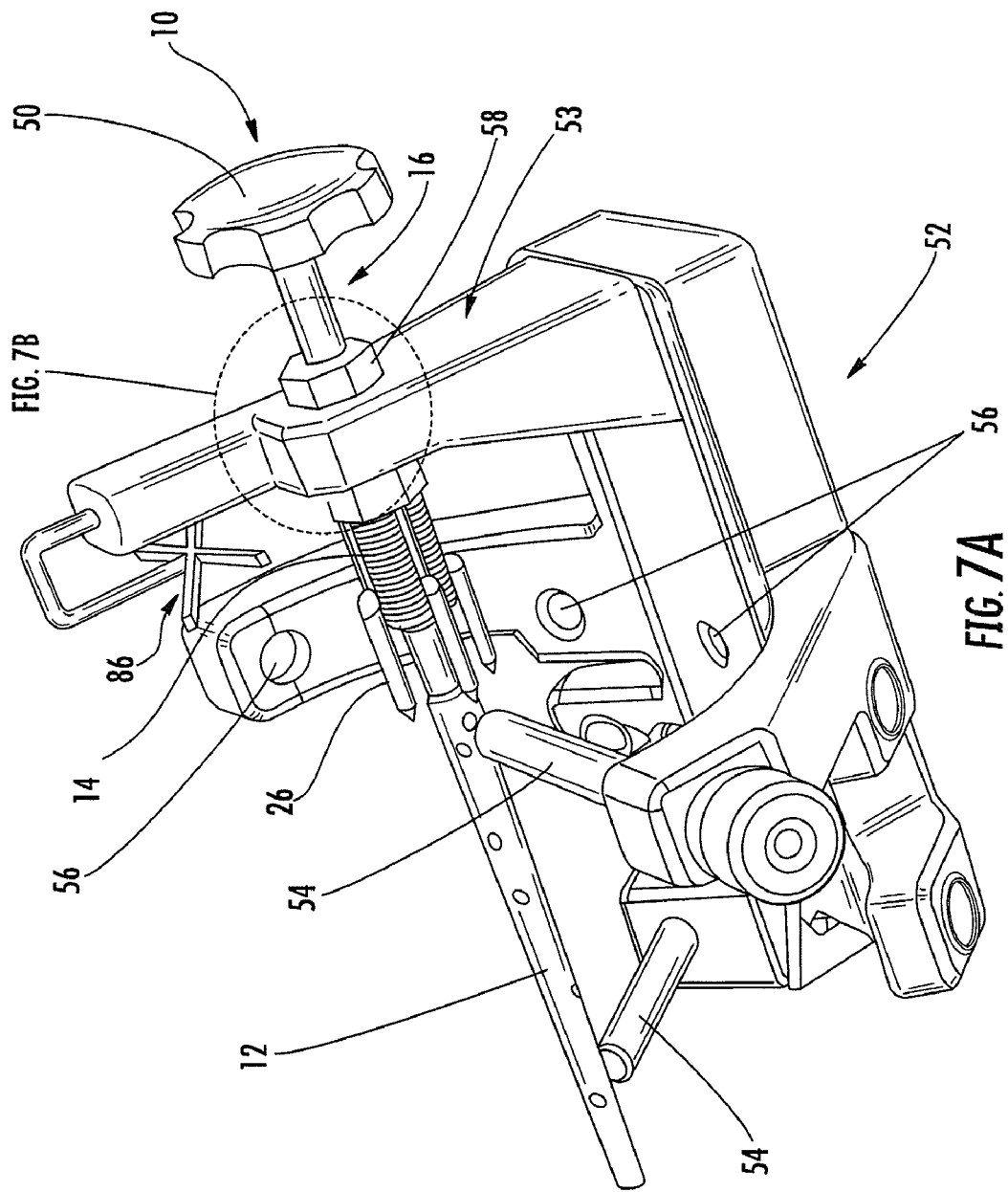

INTRAMEDULLARY DEVICE ASSEMBLY AND ASSOCIATED METHOD

FIELD OF THE INVENTION

Intramedullary devices for repairing bone defects and, more specifically, to intramedullary device assemblies for providing fixation, compression, and/or stabilization of the diaphysis or metaphysis of a long bone or periarticular bone.

BACKGROUND OF THE INVENTION

Intramedullary devices, such as nails, rods, or pins, are often used in the medical field to treat fractures of long bones, such as in the ulna and femur. These intramedullary devices also may be used to treat periarticular fractures, such as in the distal radius and proximal humerus. Such devices are typically designed to be inserted into the medullary canal of the fractured bone and generally are fastened to the bone segments on either side of the fracture to stabilize the bone and promote proper healing.

In some cases, the bone segments on either side of a fracture are spaced apart and must be brought closer together at the fracture to promote healing. Devices have been proposed that provide compression to such bone fractures by fixing the intramedullary device to one bone segment and then moving the free bone segment towards the fixed bone segment by way of compression applied to the end of the free bone segment. The free bone segment is then secured to the intramedullary device and the fracture is allowed to heal. However, these compression providing devices must be securely and removably attached to the intramedullary device while not compromising the integrity of the intramedullary device or the ability of the compression device to provide appropriate compression. In some cases, a drill guide must also be securely and removably attached to the intramedullary device.

Thus, there remains a need for an intramedullary device assembly that is easy to install without the need for extensive surgical dissection, and provides appropriate compression of the bone to promote healing.

BRIEF SUMMARY OF THE INVENTION

The present invention generally related to an intramedullary device for repairing defects of a bone. Advantageously, in one embodiment, the intramedullary device is configured to be inserted into the medullary canal of a bone and includes a stud extending from the exposed end. The stud includes a portion that is tapered from a first, smaller cross-sectional area where the stud attaches to the intramedullary device, to a second, larger cross-sectional area. The first, smaller cross-sectional area provides a region of stress concentration. The stud also includes an externally threaded portion configured to engage the internal threads of a fastener retained within a guide adapter. The external threads of the stud engage the internal threads of the fastener to secure the intramedullary device to the guide adapter when a first torque is applied to the internally-threaded fastener. The first torque may be limited by a torque-limiting driver. Upon completion of insertion, compression and securing of the intramedullary device in the medullary canal of the bone, the intramedullary device can be separated from the guide adapter by applying a second, greater torque to the internally-threaded fastener whereby the stud breaks free of the intramedullary device at the region of concentrated stress.

In one embodiment, an intramedullary device assembly includes an intramedullary device and a guide adapter. The guide adapter includes a bone engagement member guide configured to attach to an end of the intramedullary device, a compression member, and a bone engagement member. The compression member and the bone engagement member are movable along the bone engagement member guide. The intramedullary device is configured to be inserted into the medullary canal of the bone and fastened to the bone on either side of the defect. Thus, application of force on the bone engagement member by the compression member in the direction of the bone advances the bone engagement member along the bone engagement member guide such that the bone engagement member engages the end of the bone. In some embodiments, the bone engagement member guide defines an elongated void, and the bone engagement member includes an internal part and an external part. The internal part is movably retained within the bone engagement member guide and the external part engages the bone. The compression member may be configured to apply force to the internal part of the bone engagement member while the external part transmits the compressive force to the bone. The guide adapter may, in some cases, be configured to attach to a drill guide. The guide adapter may define a keyway slot configured to permit alignment of the drill guide with respect to the intramedullary device assembly.

In one embodiment, the intramedullary device assembly includes an intramedullary device and a guide adapter. The guide adapter may include a bone engagement member guide, a compression member, and a bone engagement member. The intramedullary device is configured to be inserted into the medullary canal of the bone and fastened to the bone on either side of the defect. The bone engagement member guide is configured to attach to an end of the intramedullary device. The compression member and the bone engagement member may be configured to be movable along the bone engagement member guide. The bone engagement member includes at least two bone engagement points, where at least one bone engagement point is movable along an axis of the bone engagement member guide relative to at least one other bone engagement point and is configured to engage an end of the bone. Thus, application of force on the bone engagement member by the compression member in the direction of the bone advances the bone engagement member along the bone engagement member guide such that the at least one bone engagement point of the bone engagement member is permitted to move relative to the other at least one bone engagement point so that both bone engagement points can securely engage the end of the bone.

In some embodiments, the bone engagement member guide defines an elongated void, and the bone engagement member includes an internal part and an external part. The internal part is configured to be movably retained within the bone engagement member guide, and the external part is configured to extend outside of the bone engagement member guide and engage the end of the bone via at least one of the bone engagement points. The compression member may be configured to apply force to the internal part of the bone engagement member, and the external part of the bone engagement member may include one or more pressing elements configured to engage the end of the bone. The external part of the bone engagement member may, in some cases, include at least two pressing elements, and at least one of the pressing elements may be shorter than the other pressing elements. The guide adapter of the intramedullary device assembly may, in some cases, be configured to attach to a drill guide. The guide adapter may define a keyway slot configured to permit alignment of the drill guide with respect to the intramedullary device assembly.

In some embodiments, the intramedullary device may include a breakaway stud attached to the intramedullary device and connecting to a bone engagement member guide. The breakaway stud is configured to break away from the intramedullary device when more than a threshold amount of force is applied to the stud. In some cases, this breakaway action may occur after the bone engagement member guide has been detached from the intramedullary device; however the breakaway stud may also be configured to break away from the intramedullary device while the bone engagement member guide is still in the attached position. The breakaway stud may also be configured to fit in a corresponding recess in the bone engagement member guide where it may be engaged by a fastener to retain the breakaway stud within the bone engagement member guide. The intramedullary device may define a recess to accept an alignment tab from the bone engagement member guide. The intramedullary device may further define a nub having a circumferential lip between the breakaway stud and the intramedullary device to at least partially engage the bone engagement member guide.

One embodiment of the breakaway stud may have external threads configured to engage the internal threads of a fastener that is retained within the bone engagement member guide. The bone engagement member guide may further be configured to provide a shoulder on which the head of the internally-threaded fastener rests retaining the internally-threaded fastener within the bone engagement member guide. The threaded breakaway stud may be inserted into the bone engagement member guide and engage the internal threads of the fastener retained within the bone engagement member guide such that when the fastener is turned, the breakaway stud is drawn in to the bone engagement member guide until the intramedullary device securely abuts the bone engagement member guide. The internally-threaded fastener may be configured to receive the application of a first torque to achieve a secure fit between the intramedullary device and the bone engagement member guide. The first torque may be applied by a torque-limiting T-handle driver or device to prevent over-torquing the internally threaded fastener and breaking the breakaway stud prematurely. Once the intramedullary device is securely attached to the bone engagement member guide, the surgical procedure may commence. After the intramedullary device is securely fastened within the compressed bone; a second torque, greater than the first torque, may be applied to the internally-threaded fastener, whereupon the breakaway stud breaks away from the intramedullary device thereby disconnecting the intramedullary device from the bone engagement member guide. The second torque may be applied with a standard, non torque-limiting T-handle driver or device. Optionally, the first torque and the second torque may each be applied with a separate torque-limiting driver wherein each of the two torque limiting drivers is pre-set with the desired torque value.

The breakaway stud may be configured with a tapered base that attaches to the intramedullary device resulting in a stress concentration area at the interface of the breakaway stud and the intramedullary device. The breakaway stud may further be configured with a medial portion between the tapered base and the threaded portion. The medial portion may comprise one or more flat facets that are configured to be gripped by a tool, such as pliers, a wrench, a hexagonal socket, or a custom tool with a keyway among others, such that the threaded stud may be removed from the internally-threaded fastener of the bone engagement member guide, allowing the bone engagement member guide to be used again with another intramedullary device.

A drill guide may also be attached to the guide adapter, where the drill guide is configured to allow drilling holes through the bone that are in alignment with corresponding holes defined by the intramedullary device. Furthermore, attaching the guide adapter to the proximal end of the intramedullary device may include providing a breakaway stud at the proximal end of the intramedullary device and attaching the first end of the bone engagement member guide of the guide adapter to the breakaway stud. In some cases, the bone engagement member guide may be engaged with a lip formed on a nub defined by the proximal end of the intramedullary device, disposed between the breakaway stud and the remainder of the intramedullary device.

Another method for detaching the intramedullary device from the intramedullary assembly may include detaching the bone engagement member guide and the compression member from the intramedullary device by disengaging the internally-threaded fastener from the externally threaded breakaway stud. The breakaway stud may subsequently be disconnected from the intramedullary device by cutting, bending/snapping, or using a second internally-threaded fastener. In some embodiments, a second internally-threaded fastener may be configured to engage the breakaway stud. As the second internally-threaded fastener is tightened, the end may seat against the intramedullary device and pull the breakaway stud while pushing against the intramedullary device until the breakaway stud is separated from the intramedullary device at the region of concentrated stress.

In other embodiments, an intramedullary device and breakaway stud for attaching an intramedullary device to a guide adapter are provided. The intramedullary device is configured to be inserted into the medullary canal of a bone and fastened to the bone on either side of a defect. The breakaway stud includes a proximal portion and a distal portion, where the proximal portion is configured to engage a bone engagement member guide of the guide adapter and the distal portion is configured to engage the intramedullary device. The distal portion includes a region of concentrated stress such that force applied to the breakaway stud is focused in the region of concentrated stress and causes the breakaway stud to break at or near the region of concentrated stress, thereby detaching the breakaway stud from the intramedullary device.

In some embodiments, the proximal portion of the breakaway stud is cylindrical with a helical thread and the distal portion of the breakaway stud may be tapered. The distal portion may taper or step down to a cross-sectional area that is smaller than other cross-sectional areas of the breakaway stud to form a region of concentrated stress. Between the proximal, threaded portion and the distal, tapered portion may be a medial portion with a polygonal cross-section or a generally circular cylindrical cross-section with at least one flat facet. The section may be a rectangular cross section resulting in four facets or a hexagonal cross section resulting in six facets along the medial portion of the breakaway stud.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1A is an expanded perspective view of an intramedullary device assembly according to one embodiment;

FIG. 1B is an illustration of an intramedullary device with chamfered hole openings according to one embodiment;

FIG. 7A is a perspective view of an intramedullary device assembly with attached drill guide according to one embodiment;

DETAILED DESCRIPTION OF THE DRAWINGS

Figure 2A:
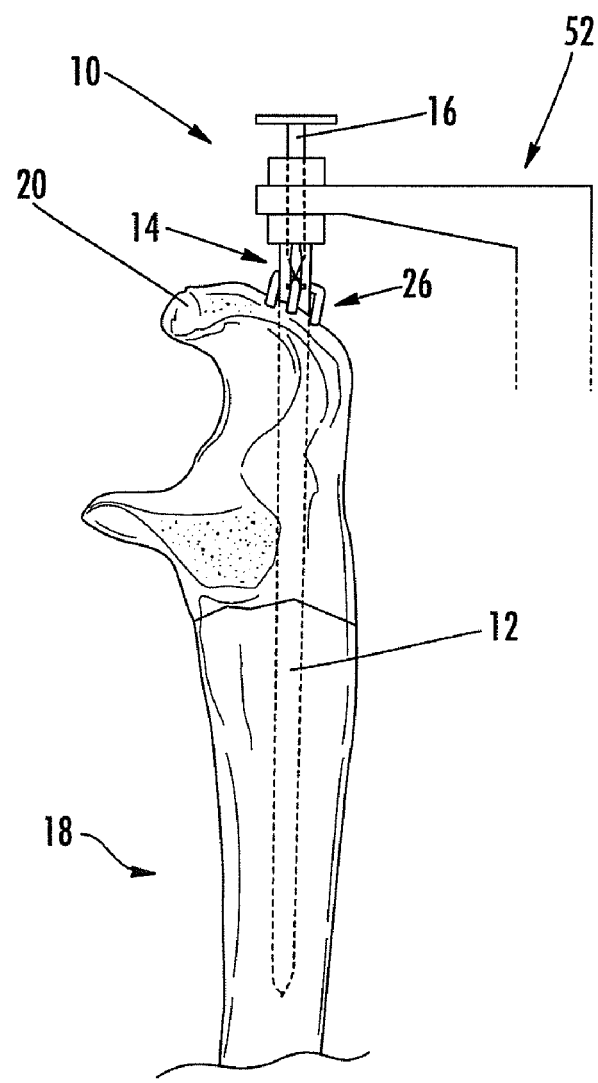
FIG. 2A is an illustration of an intramedullary device assembly installed in an ulna according to one embodiment.

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Embodiments of the present invention generally relate to an intramedullary device assembly for repairing fractures, osteotomies, and other defects of a long bone or periarticular bone. For ease of explanation, however, the specification and accompanying figures will refer to bone fractures, although it is to be understood that any type of bone repair, including the repair of fractures, osteotomies, and other bone defects, and combinations thereof, may be accomplished using embodiments of the device described herein.

As described further below, the intramedullary device assembly includes an intramedullary device that is configured to be inserted into the medullary canal of the fractured bone. A guide adapter that includes a bone engagement member guide attaches to the end of the intramedullary device and includes a movable bone engagement member configured such that a compression member attached to the guide adapter at an opposite end from the device can push the bone engagement member to engage the end of the bone. By fastening the installed intramedullary device to the bone segment on a distal side of the fracture and then applying compression via the compression member and bone engagement member, the fastened bone segment may be pushed towards the bone segment on the proximal side of the fracture. Once the desired compression is achieved, the proximal bone segment may be fastened to the intramedullary device, and the guide adapter and compression member may be detached from the device so that the patient may be able to use the affected joint to a greater extent during the healing process. In this regard, the terms "proximal" and "distal" refer to locations of the bone and assembly relative to the insertion site of the assembly after it has been inserted into the bone. In other words, the proximal side of the fracture refers to a segment of bone closer to the site at which the intramedullary device assembly was inserted; the distal side of the fracture refers to a segment of bone farther from the insertion site, and so on. Thus, for ulnar applications at the olecranon, the terms proximal and distal will coincide with those terms as used to describe the human body. However, for ankle applications, for example, the terms will be reversed.

The compression member may be pre-adjusted such that the bone engagement member may be pushed against the proximal fragment as the intramedullary device is advanced into the medullary canal, as described below. In this way, at least partial compression at the fracture site may be provided without changing the position of the intramedullary device within the proximal fragment. Also in this way, the alignment of the bone segments may be provisionally held by the bone engagement member until more definitive fasteners are placed.

Referring to FIG. 1A, an intramedullary device assembly 10 according to one embodiment is shown in an expanded view. The assembly 10 includes an intramedullary device 12, a guide adapter 14, and a compression member 16 that may be attached end-to-end to treat a fracture, as described below. The intramedullary device 12 is configured (i.e., shaped and sized) to be inserted into the medullary canal of a bone and fastened to the bone on either side of the fracture. Thus, the particular configuration of the intramedullary device 12 may vary depending on the type and size of the bone to be treated. For example, an intramedullary device 12 to be used for fixing a fracture of an adult femur may have different dimensions and may be shaped differently than a device 12 to be used for fixing a fracture of a child's radius. Furthermore, the device 12 may be made of any absorbable or non-absorbable material that is compatible for use inside the human body, such as titanium, stainless steel, cobalt chrome, plastic, carbon fiber, or polymer.

In the embodiment shown in FIG. 1A for example, the intramedullary device 12 is configured for use in an adult ulna via insertion through the olecranon. However, the intramedullary device 12 and assembly 10 may be used in various other locations in the human body, such as for repairing a fracture of the lateral malleolus (distal fibula) at the ankle. The intramedullary device 12 of FIG. 1A is tapered, with the proximal end (i.e., the end closest to the olecranon when installed) having a slightly larger diameter than the distal end (i.e., the end farthest from the olecranon when installed). Also, the intramedullary device may be tapered in the reversed manner or remain uniform in diameter throughout its length. Its axis may be straight, as shown in FIG. 1A, or curved. An ulna 18 and an olecranon 20 are illustrated in FIG. 2A, which shows an installed assembly 10 according to one embodiment. Referring again to FIG. 1A, the intramedullary device 12 may include a number of holes 22 configured to receive fasteners for fastening segments of bone to the intramedullary device 12. One or more of the holes 22 may be located towards the distal end of the intramedullary device 12, for example to fasten a bone segment that is on a distal side of the fracture to the intramedullary device 12, whereas one or more other holes 22 may be located towards the proximal end of the intramedullary device 12, for fastening another bone segment that is on a proximal side of the fracture, as discussed below. Furthermore, the holes 22 may be configured to receive various types of fasteners, such as pins, bolts, pegs, screws, and locking screws, among others. In some cases, the holes 22 may be internally-threaded to receive corresponding externally threaded fasteners. As shown in FIG. 1B, the holes 22 may have a chamfered opening 23 on the side configured to receive a corresponding fastener which may aid insertion of the fastener by providing a larger opening to accept and guide the fastener.

Figure 3:
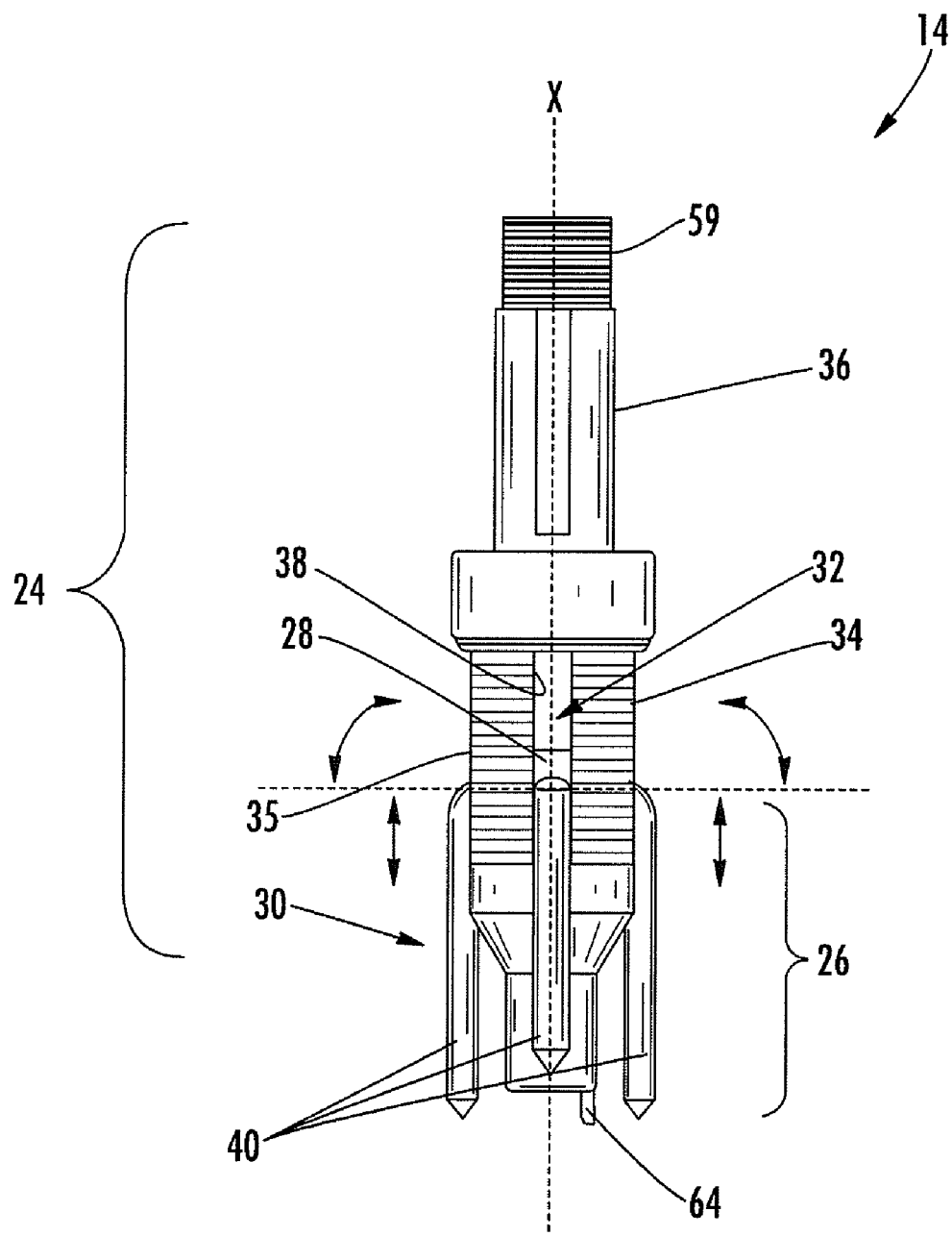
FIG. 3 is a side view of a guide adapter with pressing elements according to one embodiment.
Figure 6A:
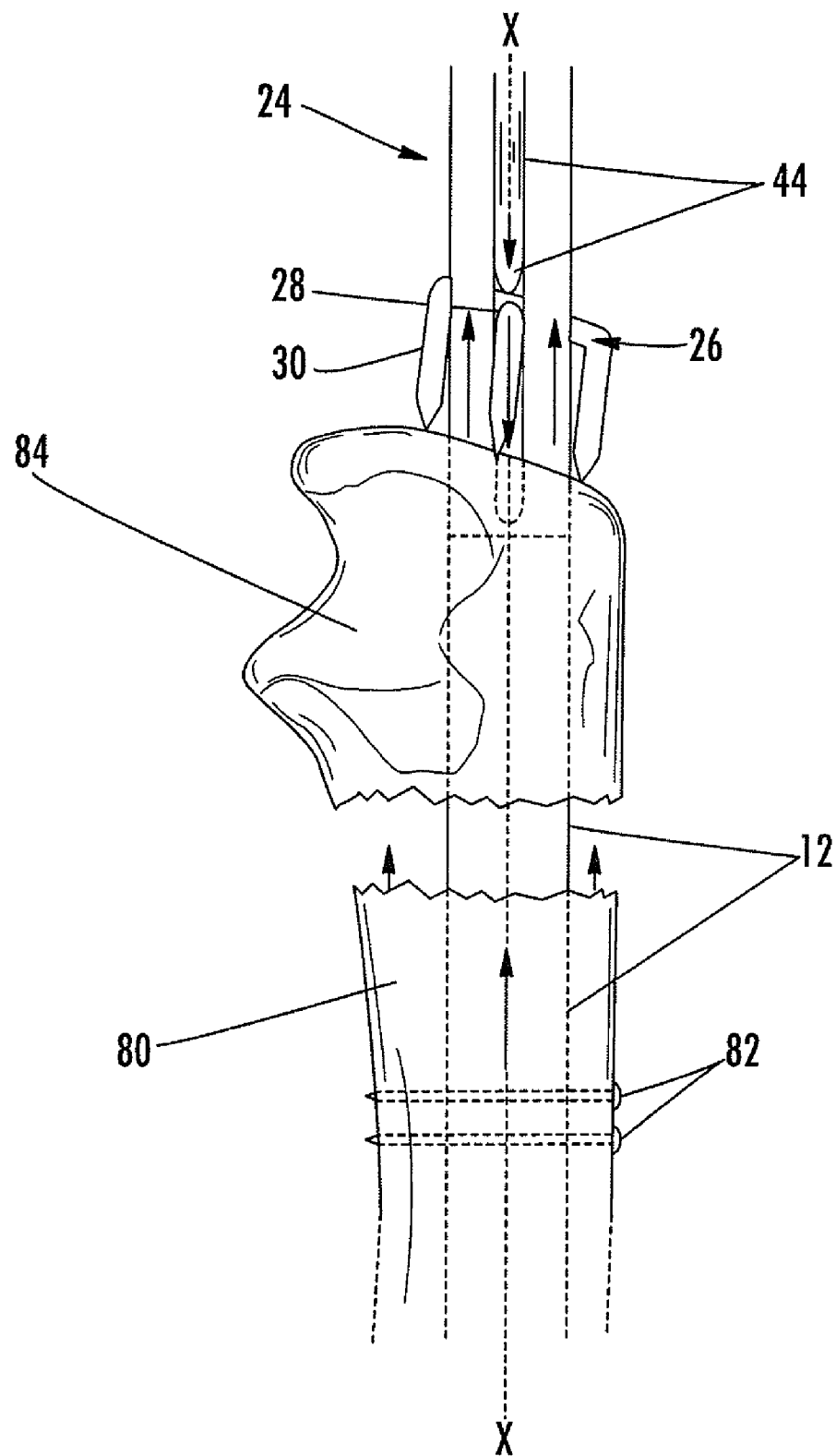
FIG. 6A is a partial side view of an installed intramedullary device assembly achieving compression according to one embodiment.

The guide adapter 14 of the assembly 10 includes a bone engagement member guide 24 and a bone engagement member 26, shown assembled according to one embodiment in FIG. 3. The bone engagement member guide 24 is configured to attach to an end of the intramedullary device 12, namely at the proximal end of the device 12, and to retain at least part of the bone engagement member 26 within the bone engagement member guide 24. For example, in the embodiment shown in FIG. 3, the bone engagement member 26 includes an internal part 28 that is configured to be movably retained within the bone engagement member guide 24 and an external part 30 that is configured to extend outside of the bone engagement member guide 24 and engage the end of the bone, as described below. In some cases, the guide adapter bone engagement member guide 24 defines an elongated void 32, such as within a cannulated portion of the bone engagement member guide, to allow the bone engagement member 26 to move along the bone engagement member guide 24. The bone engagement member guide 24 may further include a fastener such as the internally-threaded fastener 75 shown in FIGS. 9C, 10B, and 10C. The bone engagement member 26 of the guide adapter 14 is configured to engage the end of the bone into which the intramedullary device 12 is inserted, as illustrated in FIGS. 2A and 6A. It is to be understood that the bone engagement member 26 may engage directly against the bone itself, soft tissue connected to the bone, or any other material found on the surface of the bone.

The bone engagement member includes at least two bone engagement points configured to engage the end of the bone. In FIG. 3, for example, the bone engagement points comprise the ends of the pressing elements 40, which are illustrated as three prongs, and which extend from the internal part 28 of the bone engagement member 26 towards the end of the bone. However, in other embodiments, the bone engagement points may be points on a continuous surface, such as two or more points on a single bone engaging element. For example, the bone engagement member 26 could comprise a flat ring or horseshoe-shaped pad depending from the internal part 28, and at least two separate geometrical points on this pad would be movable relative to each other in an axial direction when the bone engagement member tilts relative to the bone engagement member guide 24. In any case, at least one of the bone engagement points is permitted to move axially relative to at least one other bone engagement point such that it can more easily and securely engage the bone. As noted, the bone engagement member 26 may be tiltable with respect to an axis X of the bone engagement member guide 24, such that the bone engagement member 26 may tilt in any direction in order to engage a bone surface that may not be perpendicular to the X-axis, as indicated by the curved arrows in FIG. 3. An example of this is illustrated in FIG. 6A. In other embodiments, the bone engagement points may be defined on structures that are configured to bend, rotate and/or telescope (with or without tilting) in order to engage the end of the bone in a desirable orientation so that the compression forces applied may be more balanced.

Figure 2B:
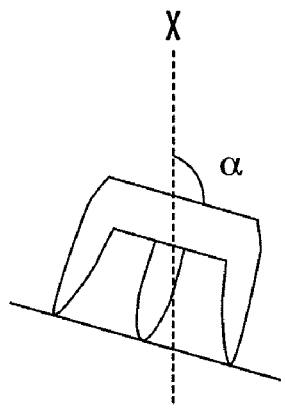
FIG. 2B shows engagement of a bone engagement member having pressing elements of equal length with a bone surface according to one embodiment.
Figure 2C:
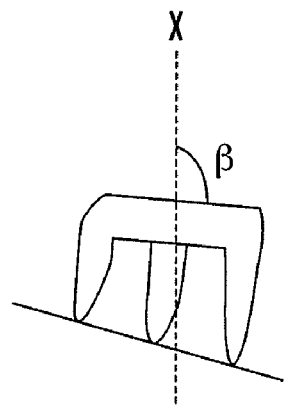
FIG. 2C shows engagement of a bone engagement member having pressing elements of unequal length with a bone surface according to another embodiment.
Figure 4:
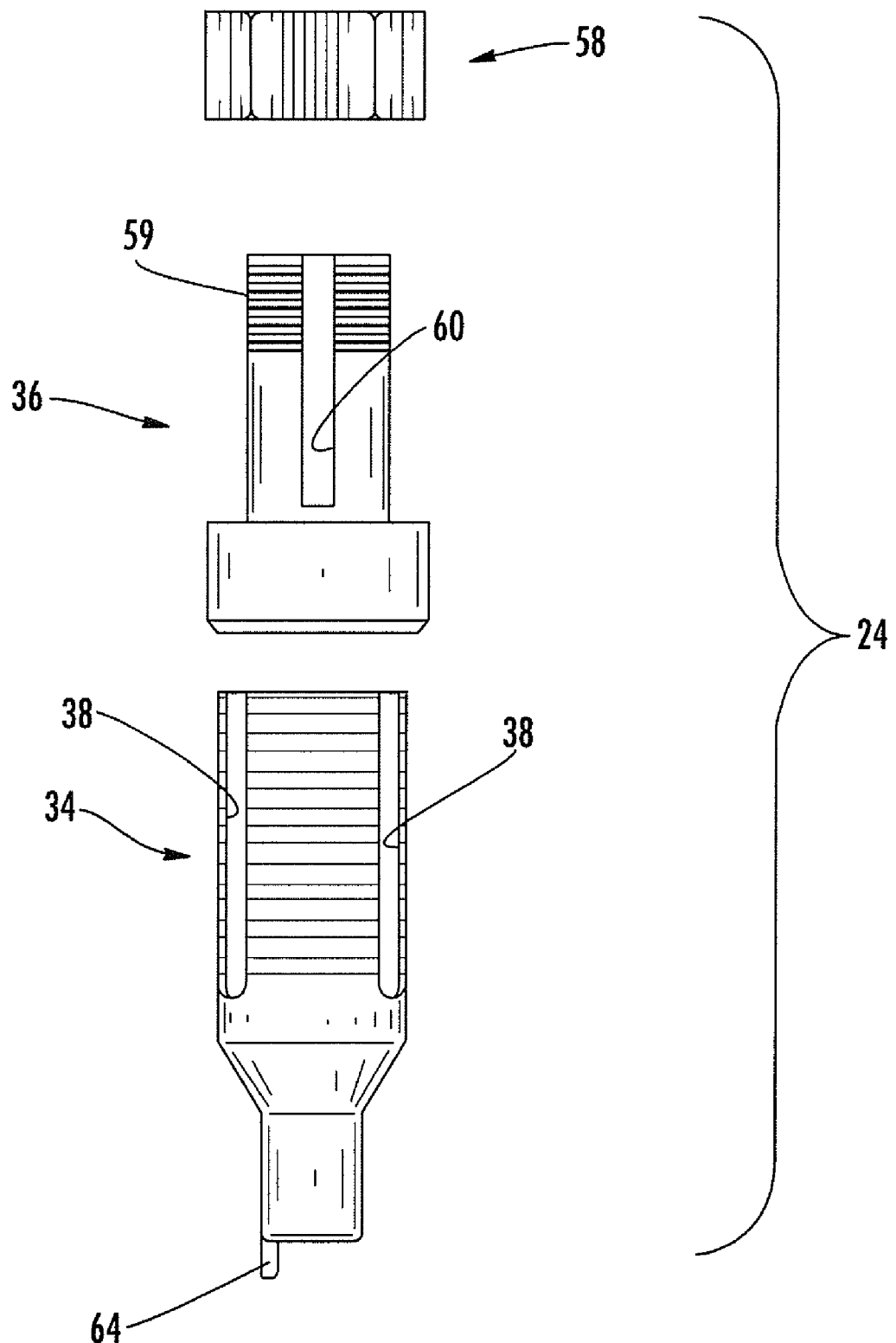
FIG. 4 is an expanded side view of a bone engagement member guide including multiple components according to one embodiment.

Referring to FIG. 4, the bone engagement member guide 24 may include more than one part that fit together or are otherwise connected to form the bone engagement member guide 24 around the bone engagement member (not shown). For example, the bone engagement member guide 24 may include a base portion 34 and an upper portion 36 that are welded together or otherwise fixedly attached after the bone engagement member 26 (shown in FIG. 3) or a portion thereof is placed within the base portion 34. In this regard, the base portion 34 may include one or more slots 38 through which the external part 30 of the bone engagement member 26 is configured to pass through. In the embodiment illustrated in FIG. 3, for example, three slots 38 (one visible) are defined in the base member 34, and the external part 30 of the bone engagement member 26 includes three pressing elements 40 that are configured to engage the end of the bone. Furthermore, at least one of these pressing elements 40 may be shorter than the other pressing elements in order to enhance the strength or stability of the engagement between the pressing elements and the end of the bone. In other words, differences in the length of the pressing elements may allow the pressing elements to conform to the angled surface of the bone while limiting the extent to which the bone engagement member must tilt to engage the bone. Thus, the angle of the internal part 28 of the bone engagement member 26 may remain closer to 90° with respect to the X-axis, providing for a more secure engagement with the bone. This is illustrated in FIGS. 2B and 2C, where the angle α (corresponding to pressing elements of equal length) is greater than the angle β (corresponding to pressing elements of unequal length). In other embodiments, the external part 30 may be configured differently.

The base portion 34 of the bone engagement member guide 24 may further include grooves 35 that provide a visual reference to a surgeon of how far the bone engagement member 26 has advanced towards the bone. For example, the grooves 35 may be equidistantly spaced at a certain interval, such as 1 mm apart. In this case, advancement of the bone engagement member 26 past 3 grooves would indicate that the bone engagement member 26 has advanced 3 mm.

Referring again to FIG. 1A, the compression member 16 of the assembly 10 is configured to attach to an end of the bone engagement member guide 24, opposite the end of the bone engagement member guide 24 that attaches to the intramedullary device 12. In some embodiments, the compression member 16 includes a pushing member 44, which may be integral to the compression member 16, as shown in FIG. 1A, or may be formed separately and subsequently attached to the compression member 16, for example via a welded or threaded connection. Regardless, the compression member 16 is movable along the bone engagement member guide 24 and is configured to move the bone engagement member 26 into engagement with the end of the bone (e.g., via the pushing member 44).

Figure 5A:
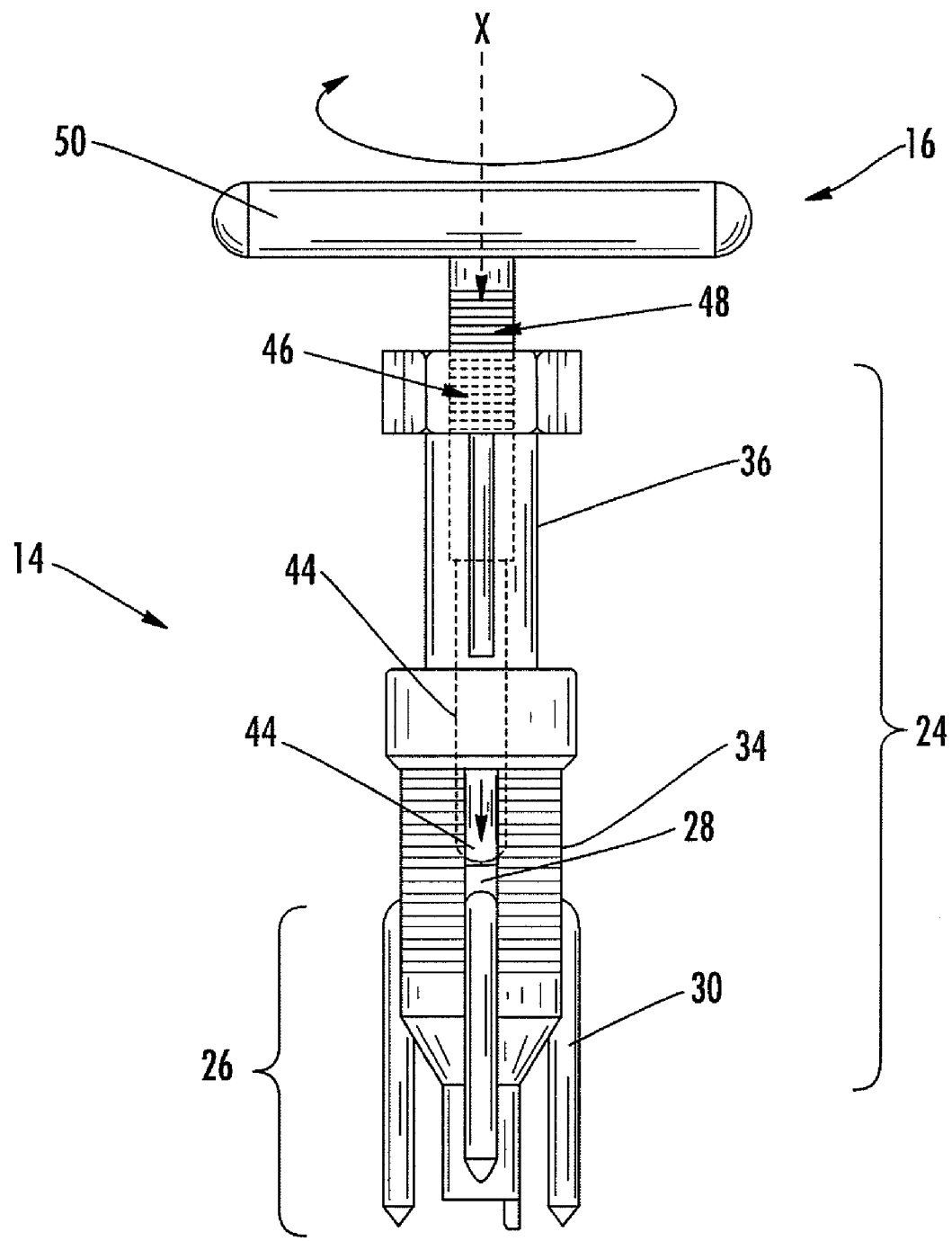
FIG. 5A is a side view of a guide adapter and compression member according to one embodiment.

For example, FIG. 5A shows a close-up view of the guide adapter 14 with the compression member 16 attached according to the embodiment illustrated in FIG. 1A. In this example, the upper portion 36 of the bone engagement member guide 24 may include an internally-threaded region 46, and the compression member 16 may include a corresponding externally threaded region 48 that is configured to mate with the internal threads 46 of the bone engagement member guide 24. In this way, rotation of the compression member 16, such as by turning a handle 50 as indicated by the arrow, would serve to advance the compression member 16 and pushing member 44 farther into the bone engagement member guide 24, towards the bone engagement member 26. The handle 50 may have various configurations. For example, the handle 50 depicted in FIG. 1A has a "T" configuration, whereas the handle 50 depicted in FIG. 7A has a knob configuration. Optionally, the pushing member 44 may be pushed with or without a compressive member 16 manually or by electronic motor through the bone engagement member guide 24 toward the bone engagement member 26. There may be a locking mechanism between the compressive member 16 and/or pushing member 44 and the bone engagement member guide 24 to maintain the position of the compression member 16 against the bone engagement member 26.

Figure 5B:
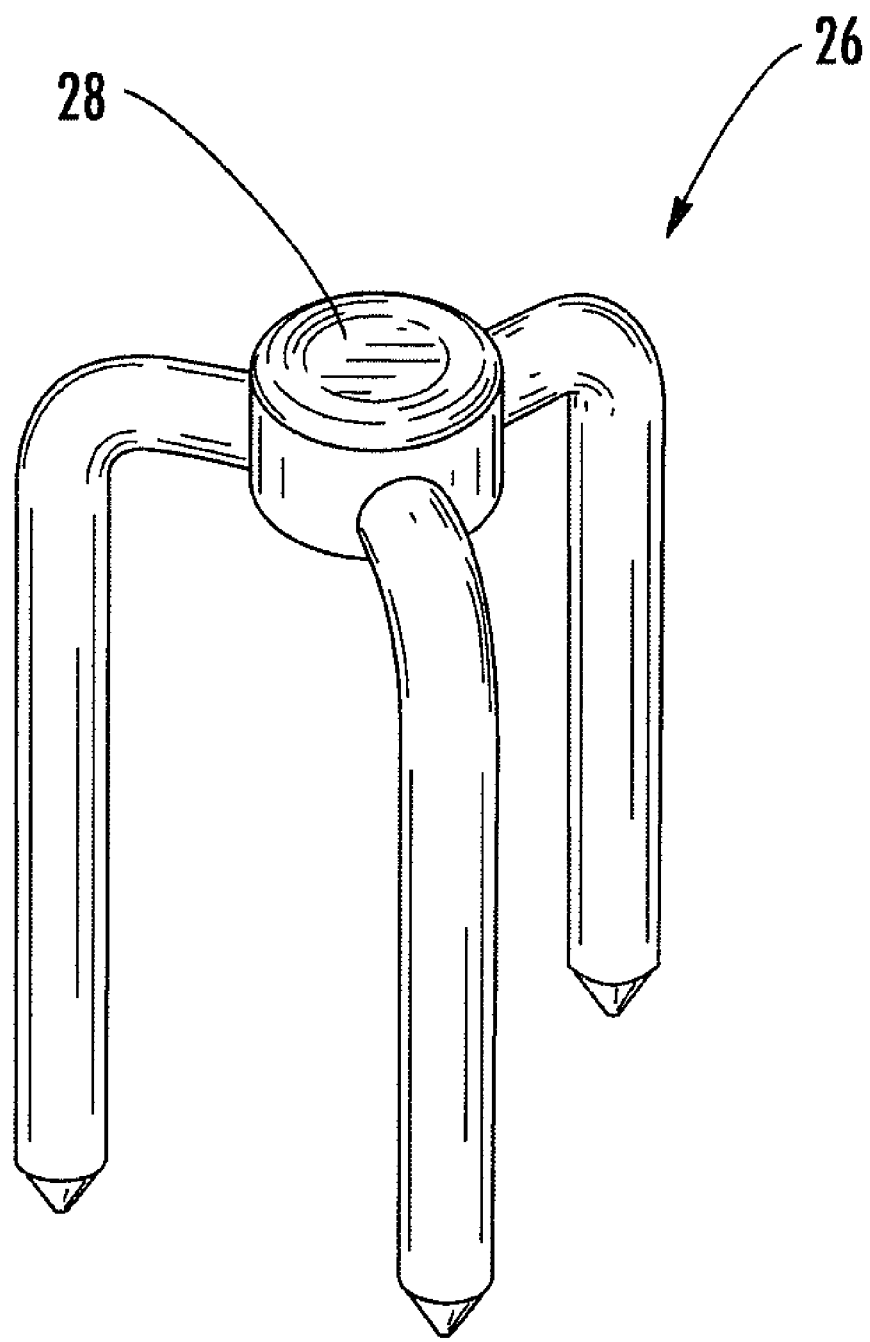
FIG. 5B is a perspective view of the bone engagement member according to the embodiment of FIG. 5A.

In an installed assembly 10 (shown in FIG. 6A), continued application of force by the pushing member 44 on the bone engagement member 26, for example, by continued rotation of the handle 50 after engagement of the bone engagement member 26 with the pushing member 44 and the bone, would serve to advance the bone engagement member 26 farther along the bone engagement member guide 24 in the direction of the intramedullary device 12. As a result, the intramedullary device 12, along with any attached bone segments, would be moved in the opposite direction (i.e., towards the compression member 16), thereby achieving compression as shown in FIG. 6A. In some embodiments, such as the one illustrated in FIG. 5A, the compression member 16 (e.g., via the pushing member 44) is configured to apply force to the internal part 28 of the bone engagement member 26. FIG. 5B shows the bone engagement member of FIG. 5A as it appears without the bone engagement member guide 24.

Figure 7C:
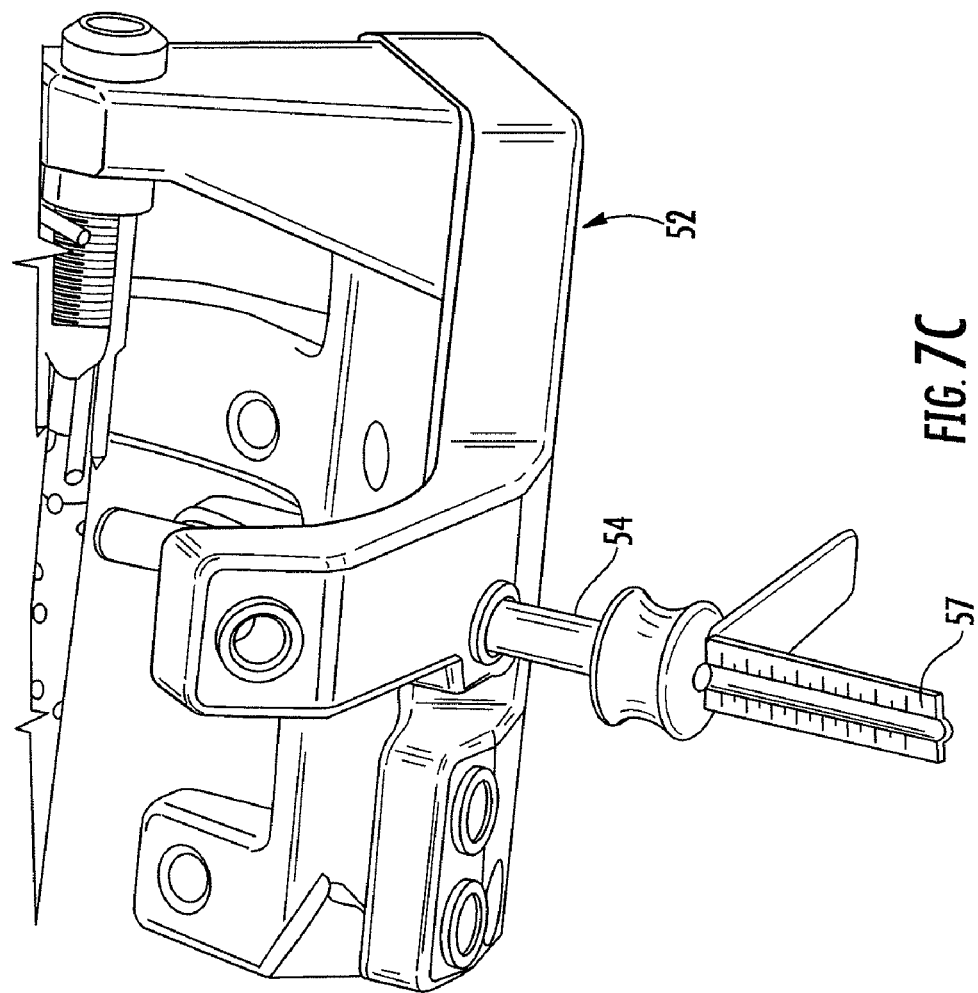
FIG. 7C is a perspective view of the drill guide with a cannula adapted to be used as a drill depth gauge.

The guide adapter 14 of the intramedullary device assembly 10 may be configured to attach to a drill guide 52, as illustrated in FIG. 7A. The drill guide 52 may be configured in various ways, depending on the configuration of the intramedullary device 12, the type of drill used (not shown), the doctor's preference, aesthetic appeal, durability and radiolucency of the materials, and other considerations. According to one embodiment, the drill guide 52 is formed of carbon fiber, though other materials, such as a radiolucent plastic material may also be used. In general, the drill guide 52 may include cannulas 54 configured to guide the drill bit or other instruments used to secure fasteners to the bone in which the intramedullary device assembly 10 is installed. For example, in the treatment of a fractured ulna, the drill guide 52 may surround the patient's elbow and forearm once the assembly 10 is installed, and the drill bit may be inserted through a cannula 54 in order to maintain the angle at which the drill bit approaches the bone to facilitate proper drilling. Furthermore, the cannula 54 may act as a soft-tissue protector as it buries itself in the soft tissue (e.g., of the forearm) through minimally invasive puncture incisions and rests against the bone. This allows the drill bit to pass through and engage the bone without damaging the surrounding soft tissue structures. Each cannula 54 may be movable between guide holes 56 at various locations defined by the drill guide 52. In this regard, the guide holes 56 may be configured to be aligned with the holes 22 of the intramedullary device 12 (FIG. 1A), such that positioning the cannula 54 at a guide hole 56 facilitates the drilling of a hole through the bone that is aligned with a device hole 22, and a fastener may then be inserted to affix the drilled bone to the device 12. The drill guide cannulas 54 may further be configured to indicate the depth of the drill bit during the drilling operation by using depth indicating markings 57 on the cannula 54 as shown in FIG. 7C and possibly using a drill bit that is configured with depth markings that may be read at the entrance to the cannula 54.

The drill guide 52 may be attached to the guide adapter 14 in many ways. For example, referring to FIGS. 4, 7A, and 7B, the drill guide 52 may have a circular void in the connecting section 53 (shown in FIG. 7A) that is configured to slide over a corresponding part of the upper portion 36 of the bone engagement member guide 24 (shown in FIG. 4). A hex nut 58 or other type of end fastener may then be attached to the end of the upper portion 36, such as via external threads 59 on the upper portion 36 or via welding, to hold the drill guide 52 in place. Optionally, the drill guide 52 and the guide adapter 14 may be fabricated from single piece of material so that the drill guide 52 and guide adapter 14 are monolithic, rather than separately connected parts.

Figure 7B:
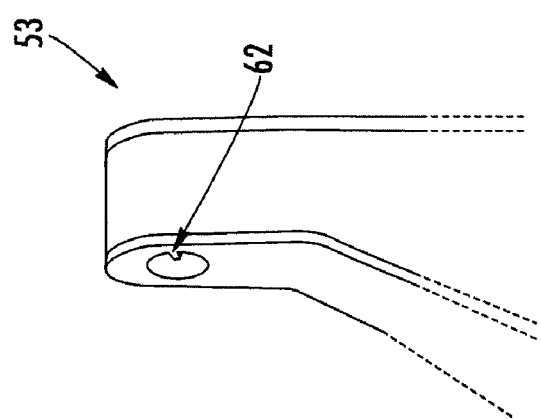
FIG. 7B is a close-up perspective view of a connecting section of the drill guide of FIG. 7A.
Figure 8:
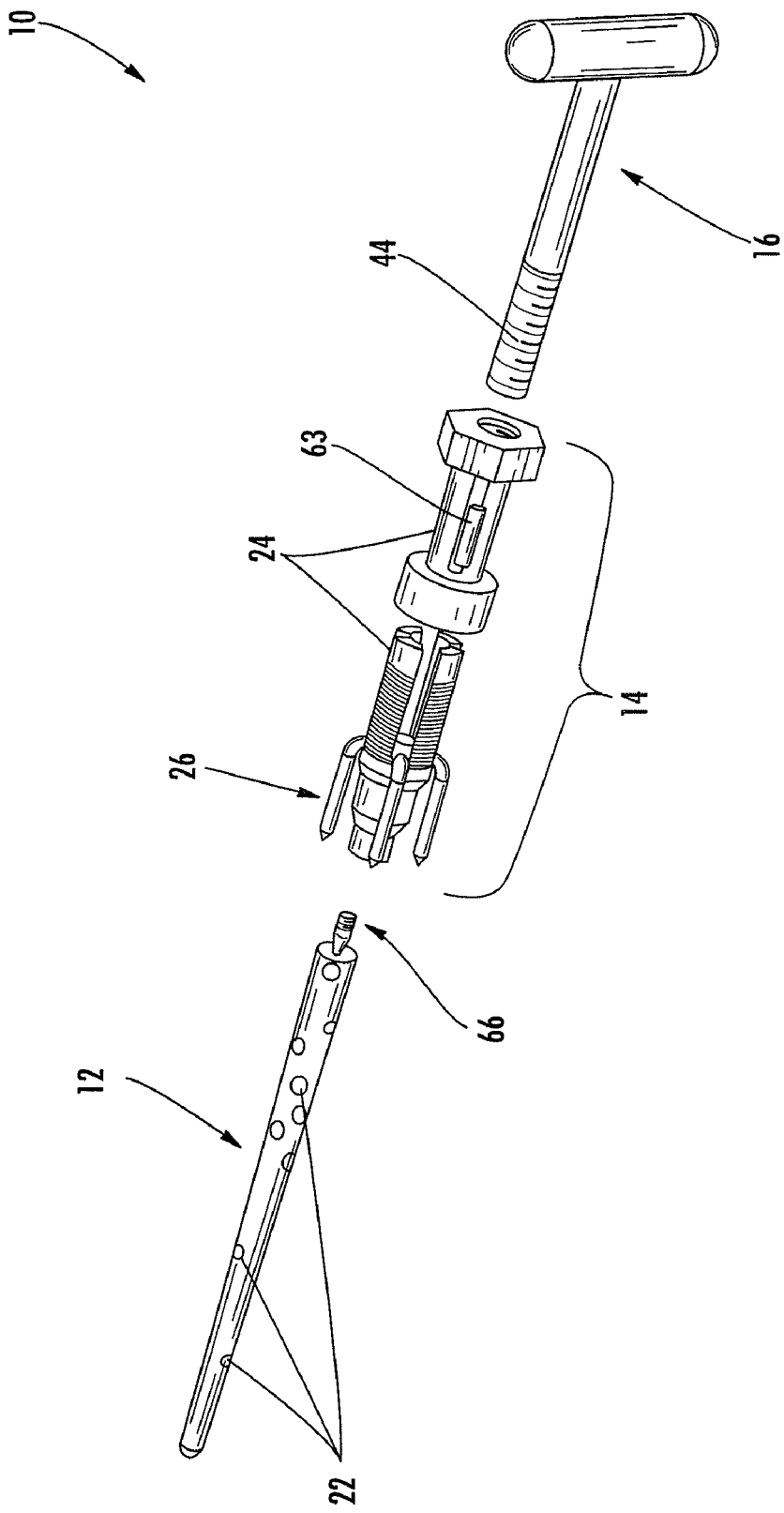
FIG. 8 is an expanded perspective view of an intramedullary device assembly including a breakaway stud according to one embodiment.

Furthermore, the bone engagement member guide 24 may define a keyway slot 60 (FIG. 4), for example in the upper portion 36, that is configured to permit alignment of the drill guide with respect to the bone engagement member guide 24 and the assembly 10 in general. In this case, the drill guide 52 would have a corresponding extension 62 formed in the void of the connecting section 53 (rather than a perfectly circular void for sliding onto the upper portion 36), as shown in FIG. 7B, that is configured to fit into the keyway slot 60 such that the drill guide 52 will only be received by the upper portion 36 in the proper orientation (i.e., with the extension 62 aligned to fit into the keyway slot 60). Alternatively, a separate adapter key 63 in the form of a rectangular bar, as shown in FIGS. 1A and 8, may be provided to prevent rotation of the guide adapter 14 relative to the drill guide 52. In this regard, a rectangular cross-section groove or slot that is aligned with the axis of the guide adapter 14 is milled in the outside surface of upper portion of the guide adapter 14. A corresponding slot is milled or broached into the drill guide 52 to be affixed to the guide adapter 14. The adapter key 63 may then be put into the slot of the guide adapter 14 such that is protrudes from the surface, as shown in the figures, and is able to engage the corresponding slot in the drill guide 52, thereby preventing rotation of the guide adapter 14 relative to the drill guide 52.

In some cases, such as in the embodiment of FIG. 7A, the drill guide 52 may include an external rotation guide 86 to provide a surgeon with a way to determine whether the intramedullary device 12 is being inserted into the medullary canal in the proper rotational orientation. If the device 12 is not at the proper rotation, some of the fasteners may be placed in suboptimal (or even deleterious) positions with respect to certain fracture types. The external rotation guide 86 may, for example, have an "X" configuration such that it may be used on different bones in the body. For instance, installing the intramedullary device 12 on a right elbow may require the surgeon to use one of the lines of the "X" for alignment, whereas installing the intramedullary device 12 on a left elbow may require the surgeon to use the other line. The cross-members of the "X" may be of square or rectangular cross section allowing an identifier such as "right" or "left" to be printed or etched onto each of the cross-members. Once the intramedullary device 12 is inserted into the canal, prior to drilling for screws, the proper rotation may be confirmed by lining up the plane of the external rotation guide 86 with the axis between the humeral epicondyles (in this example). The axis in this case should be approximately 10° from the horizontal relative to the joint line of the ulnohumeral joint. If the device 12 is rotated inappropriately, the respective line of the "X" will appear tilted away from the axis of the epicondyles, warning the surgeon that the position of the device 12 needs readjustment prior to drilling. The external rotation guide 86 may be removable (e.g., if the surgeon prefers other methods of confirming rotational alignment), and the position of the external rotation guide 86 may be adjustable such that it may be raised or lowered to correspond to the humeral epicondylar axis of the particular patient.

Figure 10A:
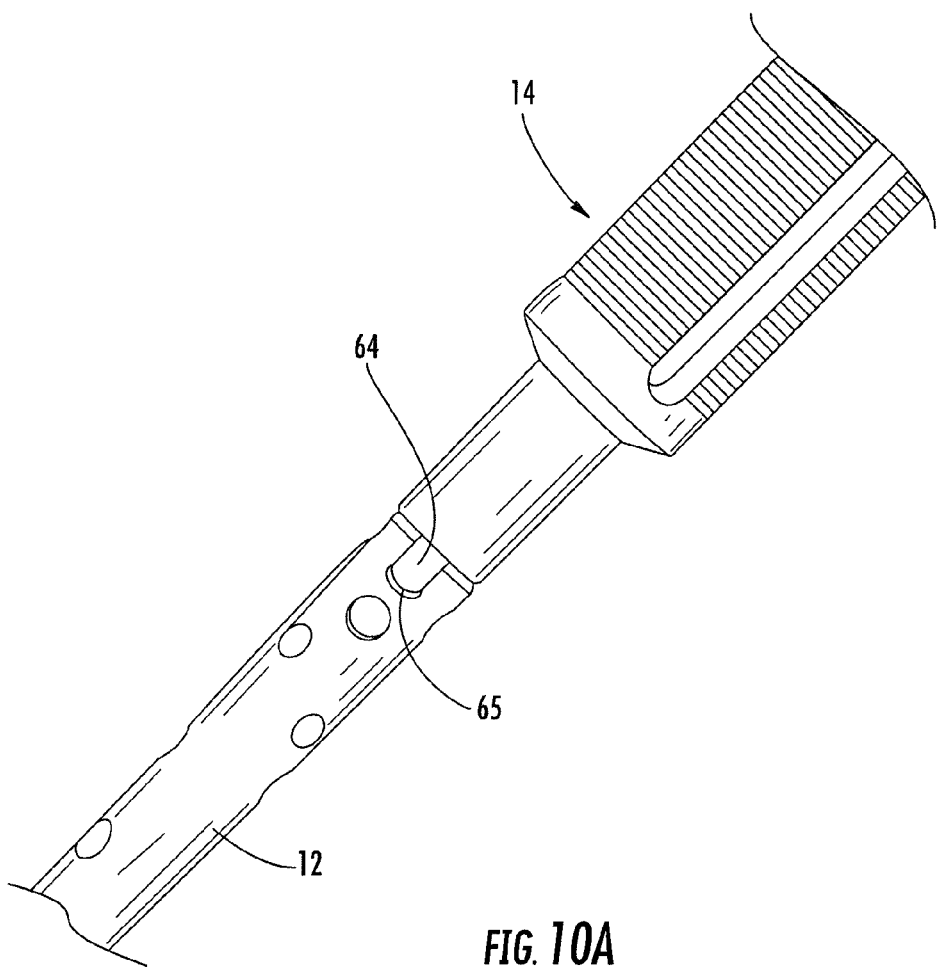
FIG. 10A is a perspective view of the intramedullary device and guide adapter showing the tab of the guide adapter according to one embodiment.

Referring to FIGS. 3, 4, and 10A, the guide adapter 14 may also include a tab 64 or other protrusion configured to engage the intramedullary device 12 to limit rotation of the guide adapter 14 with respect to the intramedullary device 12. In this regard, the tab 64 may be configured to fit in a corresponding recess 65 in the attachment end of the intramedullary device 12 such that the guide adapter 14 and the intramedullary device 12 may only be attached when the tab 64 is aligned with the corresponding recess 65, and, once attached, torsion and bending forces across the junction may be controlled. Optionally, the intramedullary device 12 may include a tab or other protrusion configured to engage a corresponding recess in the guide adapter 14 to limit rotation of the guide adapter 14 with respect to the intramedullary device 12 and to control torsion and bending forces across the junction. When the guide adapter 14 and the intramedullary device 12 are assembled, the tab 64 and recess 65 may align the intramedullary device 12 with the guide adapter 14 and may also align a drill guide 52 such that each fastener hole 22 in the intramedullary device 12 aligns with the drill guide holes 56 as shown in FIG. 7A. The tab 64 and recess 65 may be of complimentary shape with a rounded end to aid alignment as the intramedullary device 12 and the guide adapter 14 are secured together.

Figures 9A, 9B:
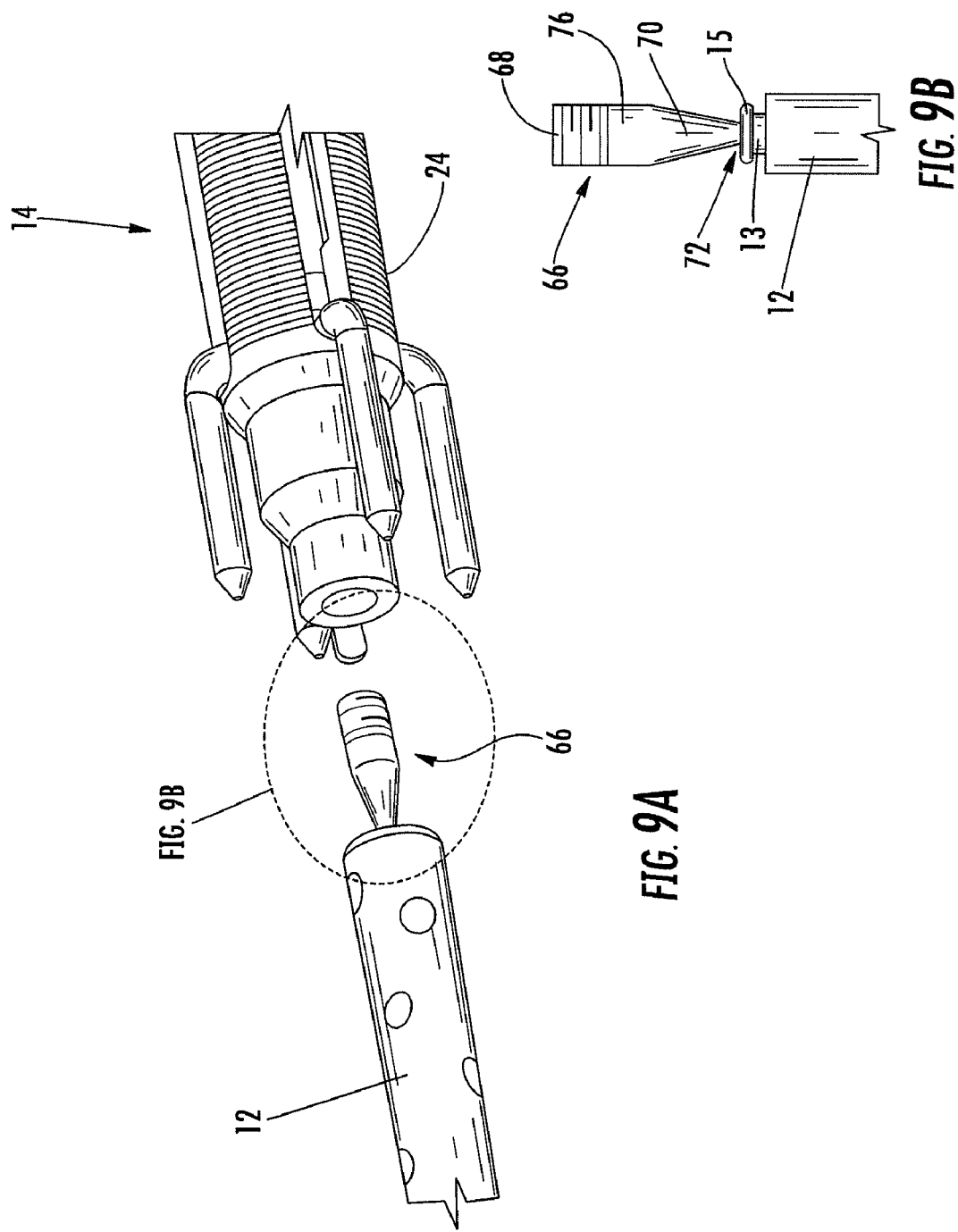
FIG. 9A is a close-up perspective view of the breakaway stud of FIG. 8.
FIG. 9B is a side plan view of the breakaway stud of FIG. 9A.
Figure 9C:
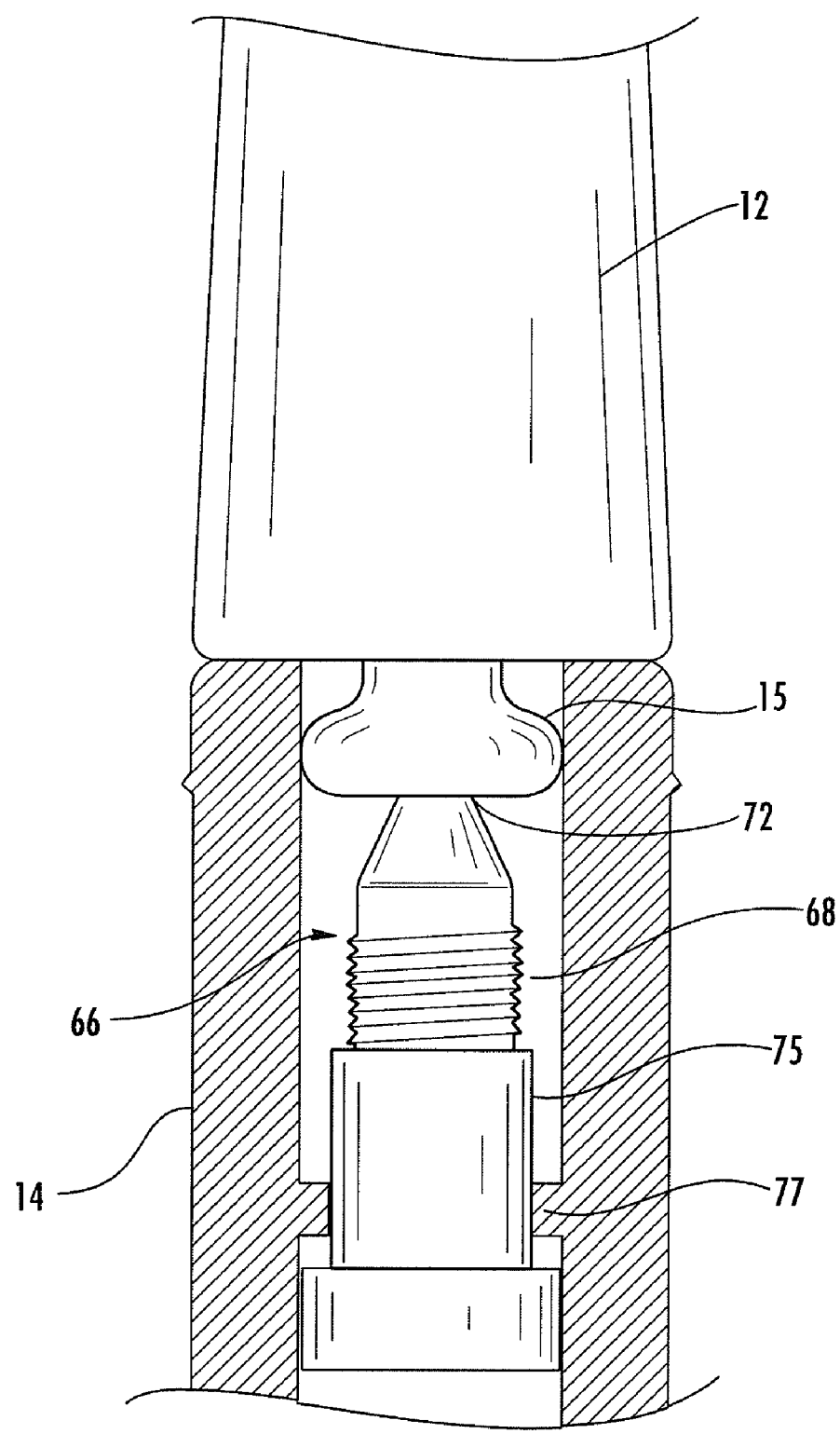
FIG. 9C is a side plan view of the breakaway stud and nub within the guide adapter.
Figure 10B:
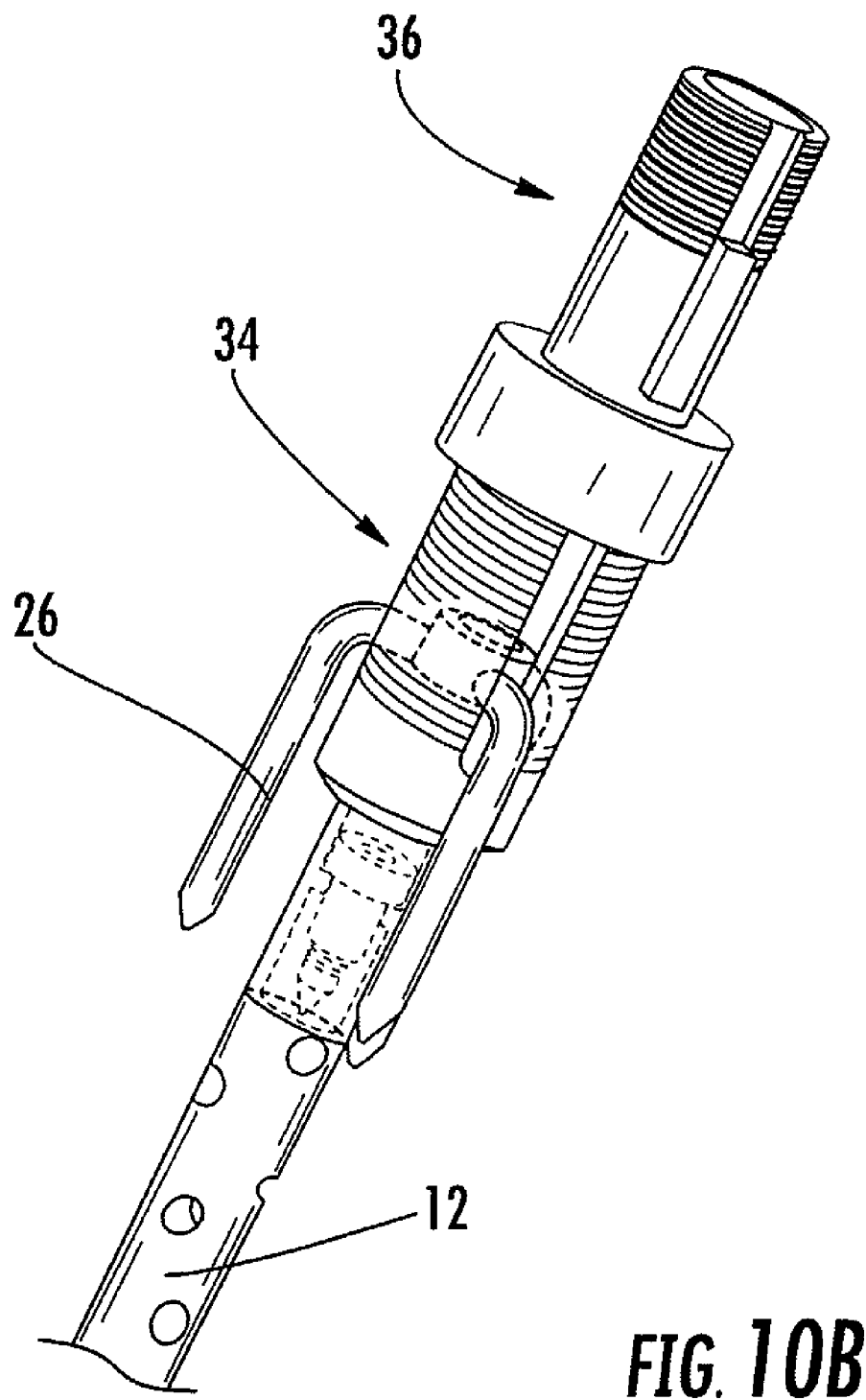
FIG. 10B is a perspective view showing the intramedullary device, breakaway stud, and guide adapter of FIG. 10A in an assembled configuration.
Figure 10C:
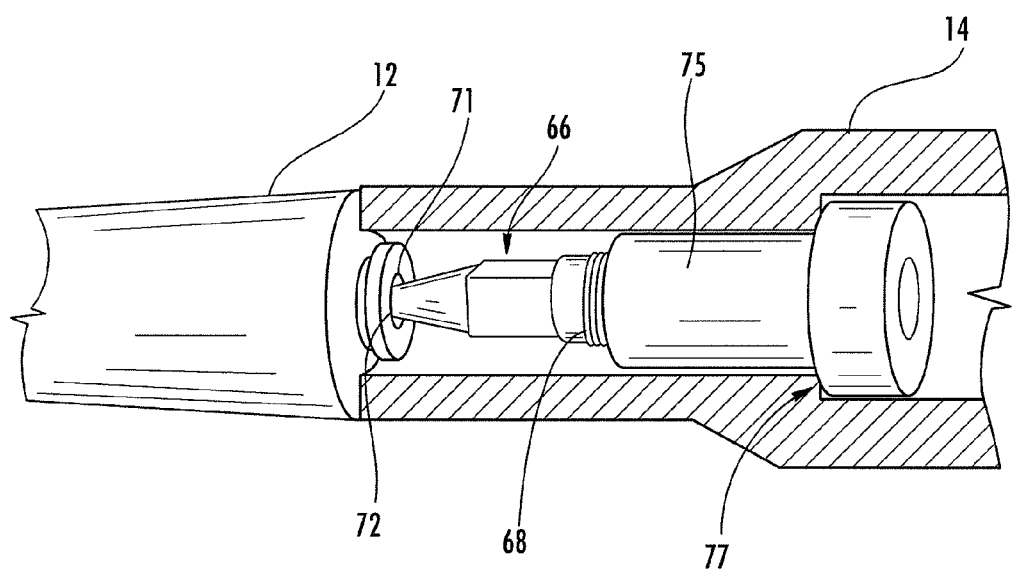
FIG. 10C is a perspective view showing the guide adapter in cross section, the internally-threaded fastener, the intramedullary device, and the breakaway stud.

In some embodiments, such as the one illustrated in FIG. 8, the intramedullary device 12 includes a breakaway stud 66 for connecting the intramedullary device 12 and the guide adapter 14. The breakaway stud 66 is configured to break away from the intramedullary device 12 when a predetermined amount of force is applied to the breakaway stud 66. Referring to FIGS. 9A and 9B, for example, the breakaway stud 66 may include a proximal portion 68, a medial portion 76, and a distal portion 70. The proximal portion 68 may have an external thread and may be configured to engage an internally-threaded fastener 75 (shown in FIGS. 9C and 10C) retained within the bone engagement member guide 24. A driving device (not shown) may be inserted through the guide adapter 14 to engage the head of the internally-threaded fastener 75. A first torque can then be applied to the internally-threaded fastener 75, and the intramedullary device 12 may be secured to the guide adapter 14 as illustrated in FIGS. 9C, 10A, 10B, and 10C. The first torque may be limited by a torque-limiting T-handle driver or device to prevent over-torquing of the internally threaded fastener. As shown in FIGS. 9C and 10C, a shoulder 77 may be provided within the bone engagement member guide 24 such that as the fastener 75 is tightened, the head of the internally-threaded fastener 75 may press against the shoulder 77, drawing the intramedullary device 12 and the guide adapter 14 together.

The medial portion 76 of the breakaway stud 66 may be configured with at least one flat facet around the perimeter, as shown in FIG. 10C to allow a tool to engage and secure the breakaway stud 66 once the breakaway stud is removed from the intramedullary device 12. Thus the breakaway stud 66 may be disengaged from the internally-threaded fastener 75 and removed from the guide adapter 14. In this way, the internally-threaded fastener 75 and the guide adapter 14 can be used with a new intramedullary device 12 in another operation. The medial portion 76 may have any number of facets, though embodiments having either four or six facets may easily be engaged by standard tools such as pliers, a wrench, or a hexagonal socket.

The distal portion 70 may be configured to engage the intramedullary device and can include a region of concentrated stress 72 that allows the force applied to the breakaway stud 66 to be focused in the region of concentrated stress 72 and causes the breakaway stud 66 to break at or near the region of concentrated stress 72. The distal portion 70 may be configured in various ways. For example, as shown in FIG. 9B, the distal portion 70 may be conically-shaped and may be tapered. Thus, in the embodiment of FIG. 9B, the region of concentrated stress 72 may be the region where the cross-sectional area of the tapered portion 70 is smallest. The distal portion 70 may also be faceted and tapered rather than conical in shape. Alternatively, the region of concentrated stress 72 may include a "shark-bite" or other type of reduction in cross-section, and is not necessarily tapered. In this way, once the assembly 10 has been installed in the medullary canal of the fractured bone, compression of the fracture has been achieved, and the bone segments of the fracture have been fastened to the intramedullary device 12 such that the fracture can heal, a second torque may be applied to the internally-threaded fastener 75 (as shown in FIG. 9C), greater than the first torque, resulting in a pulling force across the region of concentrated stress 72 that breaks the breakaway stud 66 free from the intramedullary device 12. The second torque may be applied with a standard, non-torque-limiting T-handle driver or device and optionally, the first torque and second torque may be applied by a first torque-limiting driver and second torque-limiting driver respectively, wherein each torque-limiting driver is pre-set with the desired torque value. For example, the internally-threaded fastener 75 may be seated on the shoulder 77 within the guide adapter 14, and as the internally-threaded fastener 75 is turned, the breakaway stud 66 may be drawn into the guide adapter 14 with enough force to separate the breakaway stud 66 from the intramedullary device 12. This separates the guide adapter from the installed intramedullary device 12, leaving the intramedullary device 12 installed in the bone to facilitate healing while at the same time allowing the patient to use the affected joint and bone to the extent possible. In some embodiments, the breakaway stud 66 may be broken away before the guide adapter 14 is removed from the intramedullary nail 12.

One of ordinary skill in the art would appreciate that the second torque is greater than a threshold force where the threshold force is greater than the force required to secure the breakaway stud 66 within the guide adapter 14 (i.e., the first torque) but less than a force that would cause damage to the patient or would result in failure of the intramedullary device assembly 10 at a location other than at the region of concentrated stress 72. The threshold force may also be achieved by bending or twisting the breakaway stud 66 when the stud is not engaged with the guide adapter 14.

Figure 9D:
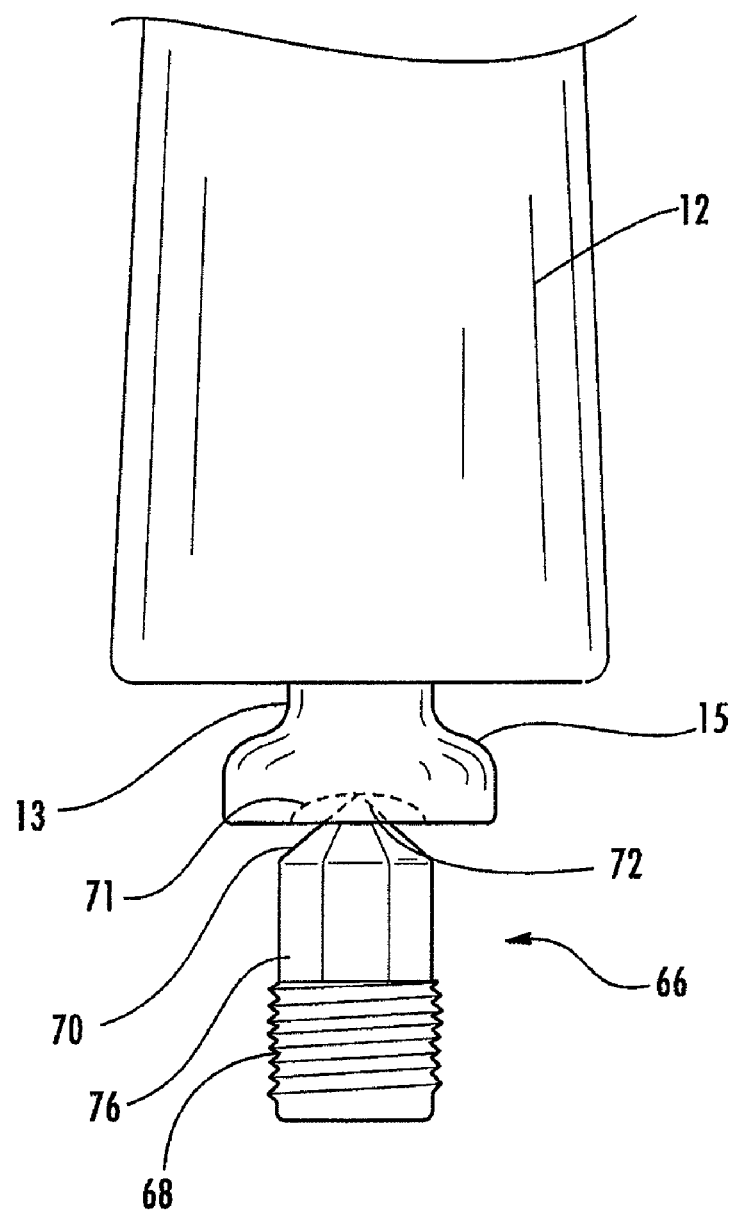
FIG. 9D is a side plan view of the breakaway stud and nub of FIG. 9C.

In some cases as shown in FIGS. 9D and 10C, the region of concentrated stress 72 may include a countersink or undercut 71 in the distal portion 70 where the breakaway stud 66 attaches to the intramedullary device 12 such that upon detachment (i.e., breaking of the breakaway stud 66), any residual portion of the stud 66 that remains attached to the intramedullary device 12 is recessed into the device 12. In this way, the residual stud is less palpable to the patient and the potential for soft tissue irritation is reduced.

In some embodiments, the proximal end of the intramedullary device 12 may define a short stump or nub 13 for attaching the breakaway stud 66, as shown in FIGS. 8 and 9B. The nub 13 may have a circumferential lip 15 that fits partially into the bone engagement member guide of the guide adapter 14 so as to offset some of the bending forces that the intramedullary device 12 may experience during installation in the bone. Furthermore, the lip 15 may allow for the intramedullary device 12 to be manipulated after installation, for example to facilitate removal of the intramedullary device 12 from the bone if removal becomes necessary or desirable. The guide adapter 14 may include a ridge 21 around the circumference, or a similar indicator, to indicate the location of the end of the nub 13 within the guide adapter 14 as shown in FIG. 9C. This ridge or marking would serve to indicate the depth to which the intramedullary device 12 must be inserted to prevent the nub 13 from protruding from the end of the bone.

In other embodiments, a method for assembling an intramedullary device assembly for repairing a defect (or defects) of a bone is provided. Referring to FIG. 1A, initially, an intramedullary device 12 configured to be inserted into a medullary canal of a bone is provided. As previously described, the intramedullary device 12 may have various configurations, depending on the location and type of bone as well as other considerations. The medullary canal of the bone may, in some cases, be prepared beforehand for receiving the intramedullary device 12 using tools and methods known by those skilled in the art, such as by drilling out the medullary canal so that the dimensions of the medullary canal correspond to the dimensions of the intramedullary device 12. The intramedullary device 12 may then be inserted into the prepared medullary canal of the bone. For example, referring to FIG. 2A, the intramedullary device 12 may be inserted into the medullary canal of a fractured ulna 18 through the metaphyseal end of ulna, or the olecranon 20. As another example, the intramedullary device 12 may be inserted into the medullary canal of a fractured fibula through the metaphyseal end of the fibula, the lateral malleolus, the medial malleous, the calcaneus, patella, or across a joint to achieve fusion. The intramedullary device may also be configured so that it cuts its own path into the bone with or without the assistance of accessory tools.

Referring again to FIG. 1A, the guide adapter 14 is attached to a proximal end of the intramedullary device 12, either before or after insertion of the intramedullary device 12 into the medullary canal. As previously described, the guide adapter 14 includes a bone engagement member guide 24 having a first end configured to attach to the proximal end of the intramedullary device 12 and a bone engagement member 26 that is movable along the bone engagement member guide 24 and includes at least two bone engagement points. At least one bone engagement point is movable along an axis of the bone engagement member guide 24 relative to at least one other bone engagement point and is configured to engage an end of the bone. For example, the bone engagement member guide 24 may be tiltable with respect to an axis X of the bone engagement member guide 24, as shown in FIGS. 2A, 2B, and 2C, or one or more of the bone engagement points may be defined on a structure, such as a discrete pressing element, that can bend, rotate, or telescope to engage the bone.

As described above, the bone engagement member guide 24 may be made up of one or more components. The bone engagement member 26 of the guide adapter 14 is configured to engage the end of a bone. For example, in FIG. 3, the bone engagement member 26 includes multiple pressing elements 40 configured to engage the surface of the end of the bone (as illustrated in FIGS. 2A and 6A). Turning again to FIG. 1A, a compression member 16, which is movable along the bone engagement member guide 24, is attached to the second end of the bone engagement member guide 24 (for example, as shown in FIG. 5A).

A drill guide 52, shown in FIG. 7A, may also be attached to the guide adapter 14, for example, as previously described with reference to FIGS. 4 and 7A. The drill guide 52 may be configured to allow the drilling of holes through the bone (i.e., through the patient's soft tissues and into the bone) such that the drilled holes are in alignment with corresponding holes defined by the intramedullary device 12. In this way, fasteners such as screws, pegs, bolts, pins or other fasteners may be inserted through the holes in the bone and received by the corresponding holes in the intramedullary device to hold the bone to the intramedullary device in those locations.

In some embodiments, such as the embodiment of FIGS. 8 and 9A, a breakaway stud 66 may be used to attach the guide adapter 14 to the proximal end of the intramedullary device 12. In this regard, one end of the breakaway stud 66 may be attached to the proximal end of the intramedullary device 12, and the other end of the breakaway stud 66 may be attached to the first end of the bone engagement member guide 24. As described above, the guide adapter 14 may be configured to engage the breakaway stud 66 by engaging an internally-threaded fastener 75 retained within the guide adapter 14 with the external threads 68 of the breakaway stud 66 as shown in FIG. 9C.

Once the intramedullary device assembly 10 is assembled and installed in the medullary canal of the affected bone, regardless of the order of the steps, compression may be applied to bring the bone segments on either side of the fracture together, thereby promoting the healing of the bone. According to one embodiment of a method of applying compression, the intramedullary device is inserted into a medullary canal of the bone, for example, as previously described. Referring to FIG. 6A, the intramedullary device 12 is fastened to a distal segment 80 of the bone (a segment located on the distal side of the bone defect relative to the intramedullary device assembly). For example, one or more locking screws 82 may be inserted through intramedullary device holes 22 (shown in FIGS. 1A and 8) to hold the distal segment 80 to the intramedullary device 12.

Compression may then be applied by advancing the compression member 16 towards the intramedullary device and bone (illustrated in FIG. 5A and indicated by the downward arrow) and into engagement with the bone engagement member 26. For example, in FIG. 5A, the handle 50 of the compression member 16 may be rotated to advance the pushing member 44 into engagement with the bone engagement member 26. As a result, the bone engagement member 26 advances towards the bone, engages the end of the bone, and continues to advance along the bone engagement member guide towards the intramedullary device 12, as illustrated in FIG. 6A, such that the distal segment 80 is moved towards the proximal segment 84 of the bone (i.e., the segment of bone located on the proximal side of the fracture relative to the intramedullary device assembly). The relative movement of the compression member 16, the bone engagement member 26, the bone engagement member guide 24, the intramedullary device 12, and the distal segment 80 are shown in FIG. 6A with arrows on the respective elements.

Figure 6B:
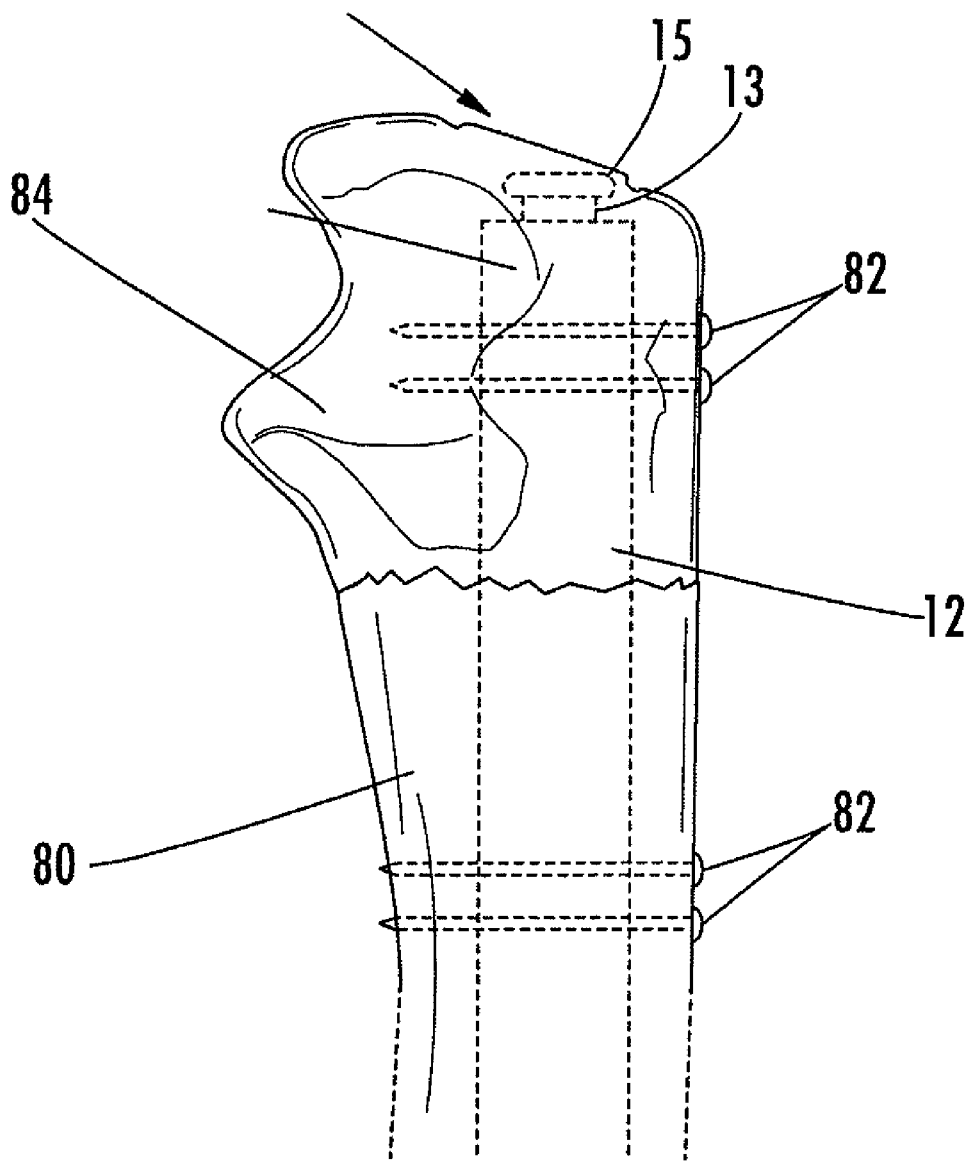
FIG. 6B is a partial side view of an installed intramedullary device of FIG. 6A after desired compression has been achieved and the guide adapter and compression member have been detached.

Referring to FIG. 6B, after the desired amount of compression has been achieved, the intramedullary device 12 may be fastened to the proximal segment 84 to maintain compression of the distal and proximal segments 80, 84. For example, screws, pegs, bolts, pins or other fasteners 82 may be inserted into holes in the intramedullary device 12, bicortically and/or unicortically, to fasten the proximal segment 84 to the intramedullary device 12. In some embodiments, the holes in the distal and/or proximal portions of the intramedullary device 12 may have internal threads (or another type of capturing mechanism) that are configured to engage external threads (or a corresponding capturing mechanism) of the fasteners. Although FIGS. 6A and 6B show the screws 82 in this example placed transversely to the device 12 and parallel to the other screws 82, the screws 82 or other fasteners may have various orientations according to the configuration of the receiving holes in the intramedullary device 12 and other considerations to allow for proper fastening between the bone and the intramedullary device 12.

In other embodiments, the proximal segment 84 may be provisionally fixed to the intramedullary assembly before compression is applied at the fracture such that compression at the fracture site may be provided without changing the position of the intramedullary device within the proximal segment. In this regard, the compression member may be pre-adjusted such that the bone engagement member is set at a pre-determined point along the guide adapter. Thus, as the intramedullary device is advanced into the medullary canal of the proximal bone segment 84, the bone engagement member is pushed against the end of the bone and the intramedullary device is placed in the correct position in the proximal segment (i.e., the proximal end of the device is aligned flush with the cortex). The entire intramedullary guide assembly may then be pushed toward the distal segment 80, while providing the ability for the surgeon to manually control and adjust the path of advancement of the proximal bone segment 84 towards the distal bone segment 80 by slight rotational or lateral movements of the intramedullary guide assembly until a desired level of initial compression is achieved at the fracture site. The position of the intramedullary device may be adjusted if necessary via the compression member. By pushing the two bone fragments together in this way, the intramedullary device assembly provisionally holds the fracture reduced until the distal screws are in place. If more compression is required, the compression member may be advanced farther along the bone engagement member guide (towards the bone). Once the appropriate amount of compression is achieved, the proximal screws may be put in place.

In any case, the guide adapter, compression member, and other attached accessories (such as the drill guide) may not be needed once the desired amount of compression has been achieved and the intramedullary device 12 has been fastened to the distal and proximal segments 80, 84 of the bone. As a result, the first end of the bone engagement member guide may be detached from the intramedullary device 12, for example by applying a second torque to the internally-threaded fastener 75 that causes the breakaway stud 66 to break free of the intramedullary device 12. In this way, the intramedullary device 12 may remain in the medullar canal of the bone, with the bone segments 80, 84 attached to facilitate stabilization of the defect and proper healing, and, at the same time, extraneous components of the assembly may be removed to provide a relatively unobstructed surface of the bone and allow the patient to use the affected part to the extent possible with greater comfort.

In embodiments that include a breakaway stud (FIGS. 8, 9A and 9B), the guide adapter 14 and the compression member 16 may be detached from the inserted and fastened intramedullary device 12 by applying a second torque to the internally-threaded fastener 75 which breaks free the breakaway stud 66 (for example, at the region of concentrated stress 72). Alternatively, the guide adapter 14 and compression member 16 may be detached from the inserted and fastened intramedullary device 12 by unthreading the internally-threaded fastener 75 from the breakaway stud 66 and disengaging the breakaway stud 66 from the guide adapter 14. The breakaway stud 66 may then be removed from the intramedullary device 12 by bending and breaking free (for example, at the region of concentrated stress 72), cutting, or using a second internally-threaded fastener that could be threaded on to the breakaway stud 66 and seat on the nub 13 or the proximal end of the intramedullary device 12 and pull the breakaway stud 66 free from the intramedullary device 12. Furthermore, if removal of the intramedullary device 12 from the bone is required at some later time, the lip 15 may be used to withdraw the intramedullary device 12 from the medullar canal, as previously discussed.

It should be appreciated that while the above described embodiments feature an external thread on the breakaway stud and an internal thread on the fastener of the guide adapter, other embodiments may have an internal thread on the breakaway stud and an external thread on the fastener retained within the guide adapter.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An intramedullary device for repairing a defect of a bone, comprising:
   an elongate body including a proximal end, a distal end, and an undercut; and
   a stud protruding from the proximal end of the elongate body configured to be removably attached to a guide adapter, the stud comprising;
   a distal portion attached to the proximal end of the elongate body; and
   a proximal portion opposite the distal portion;
   wherein at least the proximal portion of the stud comprises a threaded portion;
   wherein the distal portion defines a first cross-sectional area and a second cross-sectional area wherein the second cross-sectional area is smaller than the first cross-sectional area, wherein the undercut is proximate the second cross-sectional area, and wherein the stud is broken at the second cross-sectional area when a threshold amount of force is applied to the threaded portion.

2. The intramedullary device of claim 1, wherein the distal portion of the stud is tapered from the first cross-sectional area proximate the proximal portion of the stud to the second cross-sectional area proximate the proximal end of the elongate body.

3. The intramedullary device of claim 1 further comprising a medial portion of the stud disposed between the distal portion and the proximal portion, wherein the medial portion of the stud comprises at least one flat facet.

4. The intramedullary device of claim 1, wherein the distal portion of the stud is tapered.

5. The intramedullary device of claim 1, further comprising a nub between the stud and the proximal portion of the elongate body.

6. The intramedullary device of claim 1, wherein the threads of the breakaway stud of the intramedullary device are configured to engage a threaded fastener within a guide adapter.

7. The intramedullary device of claim 6, wherein the elongate body is configured to be secured to the guide adapter by applying a first torque to the threaded fastener.

8. The intramedullary device of claim 7, wherein the elongate body is configured to be separated from the guide adapter when the breakaway stud is broken away from the intramedullary device by a second torque applied to the threaded fastener wherein the second torque is greater than the first torque.

9. The intramedullary device of claim 8, wherein the threaded fastener comprises a fastener head that engages a shoulder within the guide adapter to retain the threaded fastener within the guide adapter.

10. The intramedullary device of claim 6, the elongate body further comprising a recess configured to engage a tab defined by the guide adapter to prevent relative rotation between the intramedullary device and the guide adapter.

11. An intramedullary device for repairing a defect of a bone, comprising:
an elongate body including a proximal end, a distal end, and an undercut; and
a stud protruding from the proximal end of the elongate body configured to be removably attached to a guide adapter, the stud comprising;
a distal portion attached to the proximal end of the elongate body wherein the distal portion defines a region configured for the concentration of stress proximate the undercut; and
a proximal portion opposite the distal portion;
wherein the stud is separated from the elongate body proximate the region configured for the concentration of stress in response to a threshold force being applied to the proximal portion of the stud.

12. The intramedullary device of claim 11, wherein the threshold force comprises a pulling force in response to the stud being drawn into the guide adapter.

13. The intramedullary device of claim 11, wherein the proximal portion comprises a threaded portion.

14. The intramedullary device of claim 11, wherein the proximal portion of the stud is engaged by a fastener within the guide adapter.

15. The intramedullary device of claim 14, wherein the fastener is configured to secure the elongate body to the guide adapter in response to a first force being applied to the fastener.

16. The intramedullary device of claim 15, wherein in response to a second force being applied to the fastener, the threshold force is applied to the proximal portion of the stud.

17. A method comprising:
applying a first torque to a fastener within a guide adapter to engage a stud of an elongate body of an intramedullary device, wherein the stud is attached to the intramedullary device proximate an undercut;
applying a second torque to the fastener within the guide adapter to cause the stud of the elongate member to be separated from the elongate member;
wherein the stud is separated from the elongate body proximate the undercut at a region configured for the concentration of stress.

18. The method of claim 17, wherein the region configured for the concentration of stress comprises a portion of the stud with the smallest cross-sectional area.

* * * * *